US012746330B2

(12) United States Patent
Cowan et al.

(10) Patent No.: US 12,746,330 B2
(45) Date of Patent: Sep. 29, 2026

(54) FLUID PATHS FOR ANGIOGRAPHY INJECTOR ASSEMBLY

(71) Applicant: BAYER HEALTHCARE LLC, Whippany, NJ (US)

(72) Inventors: Kevin Cowan, Allison Park, PA (US); John Haury, Sewickley, PA (US); James Dedig, Pittsburgh, PA (US); Gerald Callan, Cranberry Township, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1027 days.

(21) Appl. No.: 17/910,938

(22) PCT Filed: Mar. 15, 2021

(86) PCT No.: PCT/US2021/022321
§ 371 (c)(1),
(2) Date: Sep. 12, 2022

(87) PCT Pub. No.: WO2021/188416
PCT Pub. Date: Sep. 23, 2021

(65) Prior Publication Data

US 2023/0146744 A1 May 11, 2023

Related U.S. Application Data

(60) Provisional application No. 62/990,141, filed on Mar. 16, 2020, provisional application No. 62/990,179, filed on Mar. 16, 2020.

(51) Int. Cl.
*A61M 5/145* (2006.01)
*A61M 5/00* (2006.01)
(Continued)

(52) U.S. Cl.
CPC ........ *A61M 5/14546* (2013.01); *A61M 5/007* (2013.01); *A61M 5/1422* (2013.01); *A61M 5/365* (2013.01)

(58) Field of Classification Search
CPC .... A61M 5/36; A61M 5/365; A61M 5/14546; A61M 5/16827; A61M 2206/14;
(Continued)

(56) References Cited

U.S. PATENT DOCUMENTS 352,715 A 11/1886 Sandmark
508,584 A 11/1893 Stevens
(Continued)

FOREIGN PATENT DOCUMENTS

CN 103917269 A 7/2014
CN 105521533 A 4/2016
(Continued)

OTHER PUBLICATIONS

"International Preliminary Report on Patentability from PCT Application No. PCT/US2021/022321", Sep. 29, 2022.
(Continued)

*Primary Examiner* — Nilay J Shah
(74) *Attorney, Agent, or Firm* — Joseph L. Kent; James R. Stevenson

(57) ABSTRACT

A fluid injector system includes at least one syringe configured for injecting medical fluid and a fluid path assembly in fluid communication with the at least one syringe, the fluid path assembly including at least one air detection region. The system includes an air detector configured to detect one or more air bubbles in a fluid path associated with the air detection region, at least one shutoff valve at a distal end of the fluid path assembly, and at least one processor programmed or configured to actuate the shutoff valve in response to the air detector detecting the one or more air
(Continued)

bubbles in the fluid path associated with the air detection region to prevent fluid flow out of the fluid path assembly. The fluid path assembly has a length greater than a distance that an air bubble can travel or expand during an actuation time of the shutoff valve.

16 Claims, 12 Drawing Sheets

(51) Int. Cl.
*A61M 5/142* (2006.01)
*A61M 5/36* (2006.01)
(58) Field of Classification Search
CPC ........ A61M 2005/1787; A61M 5/2066; A61M 5/2448; A61M 5/31596; A61M 5/1407; A61M 5/1408
See application file for complete search history.

(56) References Cited

U.S. PATENT DOCUMENTS 798,093 A 8/1905 Edward
817,054 A 4/1906 Daniel
937,029 A 10/1909 Blessing et al.
945,143 A 1/1910 Iacques
1,388,946 A 8/1921 Goold
1,930,929 A 10/1933 Joel et al.
2,062,285 A 12/1936 Sam et al.
2,511,291 A 6/1950 Mueller
2,514,575 A 7/1950 Hein et al.
2,583,206 A 1/1952 Borck et al.
2,592,381 A 4/1952 Blackman
2,616,422 A 11/1952 Jones
2,667,163 A 1/1954 Smith
2,667,164 A 1/1954 Smith
2,667,165 A 1/1954 Smith
2,667,872 A 2/1954 Smith
2,672,866 A 3/1954 Kater
2,673,561 A 3/1954 Peterson, Jr.
2,688,963 A 9/1954 Smith
2,688,964 A 9/1954 Smith
2,690,179 A 9/1954 Fox
2,717,598 A 9/1955 Krasno
2,805,662 A 9/1957 Lawshe et al.
2,911,972 A 11/1959 Elinger
2,915,986 A 12/1959 Sisson
2,935,067 A 5/1960 Bouet
2,950,717 A 8/1960 Bonet
3,101,712 A 8/1963 Strazdins et al.
3,155,281 A 11/1964 Stracey
3,159,312 A 12/1964 Van Sciver, II
3,161,194 A 12/1964 Chapman
3,161,195 A 12/1964 Taylor et al.
3,166,070 A 1/1965 Everett
3,172,577 A 3/1965 Hartung
3,190,619 A 6/1965 Penney et al.
3,199,511 A 8/1965 Kulick
3,231,139 A 1/1966 Bouet
3,276,472 A 10/1966 Jinkens et al.
3,301,293 A 1/1967 Santelli
3,340,869 A 9/1967 Bane
3,353,537 A 11/1967 Knox et al.
3,390,821 A 7/1968 Mullan
3,411,503 A 11/1968 Santomieri
3,412,906 A 11/1968 Dinger
3,442,424 A 5/1969 Sam et al.
3,471,058 A 10/1969 Peter et al.
3,473,524 A 10/1969 John
3,474,844 A 10/1969 Rudolph et al.
3,506,163 A 4/1970 Rauh et al.
3,507,278 A 4/1970 Winfried
3,527,215 A 9/1970 De Witt
3,557,788 A 1/1971 Swartz
3,581,475 A * 6/1971 Sauder .................... E21B 36/00
165/275
3,613,963 A 10/1971 Berkmuller
3,618,846 A 11/1971 Poli
3,635,444 A 1/1972 Potter
3,671,208 A 6/1972 Medsker
3,699,961 A 10/1972 Szpur
3,719,207 A 3/1973 Takeda
3,736,932 A 6/1973 Satchell
3,785,367 A 1/1974 Fortin et al.
3,826,409 A 7/1974 Chilcoate
3,868,967 A 3/1975 Harding
3,873,003 A 3/1975 Seiferth et al.
3,938,514 A 2/1976 Boucher
3,942,528 A * 3/1976 Loeser .................. A61M 39/04
604/86
3,998,223 A 12/1976 Dawe
4,035,461 A 7/1977 Korth
4,041,944 A 8/1977 Rhodes
4,044,836 A 8/1977 Martin et al.
4,064,879 A 12/1977 Leibinsohn
4,066,080 A 1/1978 Sneider
4,131,217 A 12/1978 Sandegren
4,136,802 A 1/1979 Mascia et al.
4,140,117 A 2/1979 Buckles et al.
4,171,698 A 10/1979 Genese
4,204,775 A 5/1980 Speer
4,208,136 A 6/1980 King et al.
4,236,516 A 12/1980 Nilson
4,245,655 A 1/1981 Patel
4,312,344 A 1/1982 Nilson
4,318,400 A 3/1982 Peery et al.
4,325,369 A 4/1982 Nilson
4,329,067 A 5/1982 Goudy, Jr.
4,349,129 A 9/1982 Amneus
4,392,491 A 7/1983 Takasugi et al.
4,411,656 A 10/1983 Cornett, III
4,419,096 A 12/1983 Leeper et al.
4,438,845 A 3/1984 Mochow
4,441,823 A 4/1984 Power et al.
4,444,310 A 4/1984 Odell
4,526,296 A 7/1985 Berger et al.
4,610,665 A 9/1986 Matsumoto et al.
4,741,733 A 5/1988 Winchell et al.
4,747,839 A 5/1988 Tarello et al.
4,753,638 A 6/1988 Peters
4,773,458 A 9/1988 Touzani
4,824,145 A 4/1989 Carlsson
4,850,807 A 7/1989 Frantz
4,895,570 A 1/1990 Larkin
4,904,239 A 2/1990 Winchell et al.
4,952,068 A 8/1990 Flint
4,969,879 A 11/1990 Lichte
5,000,739 A 3/1991 Kulisz et al.
5,011,477 A 4/1991 Winchell et al.
5,026,348 A 6/1991 Venegas
5,033,631 A 7/1991 Nightingale
5,048,684 A 9/1991 Scott
5,120,315 A 6/1992 Hessel
5,147,311 A 9/1992 Pickhard
5,163,928 A 11/1992 Hobbs et al.
5,178,610 A 1/1993 Tsujikawa et al.
5,192,272 A 3/1993 Faure
5,199,567 A 4/1993 Discko, Jr.
5,201,438 A 4/1993 Norwood
5,209,372 A 5/1993 Norwood
5,236,204 A 8/1993 Hempel
5,237,309 A 8/1993 Frantz et al.
5,238,003 A 8/1993 Baidwan et al.
5,238,150 A 8/1993 Williams
5,240,130 A 8/1993 Osbakk
5,242,422 A 9/1993 Schneberger et al.
5,263,940 A 11/1993 Kriesel
5,269,428 A 12/1993 Gilbert
5,312,018 A 5/1994 Evezich
5,316,452 A 5/1994 Bogen et al.
5,318,520 A 6/1994 Nakao
5,318,540 A 6/1994 Athayde et al.
5,333,761 A 8/1994 Davis et al.

(56) References Cited

U.S. PATENT DOCUMENTS

| | | | |
|---|---|---|---|
| 5,342,313 | A | 8/1994 | Campbell et al. |
| 5,353,961 | A | 10/1994 | Debush |
| 5,370,250 | A | 12/1994 | Gilbert |
| 5,383,858 | A | 1/1995 | Reilly et al. |
| 5,397,157 | A | 3/1995 | Hempel et al. |
| 5,399,173 | A | 3/1995 | Parks et al. |
| 5,431,185 | A | 7/1995 | Shannon et al. |
| 5,492,147 | A | 2/1996 | Challender et al. |
| 5,507,535 | A | 4/1996 | McKamey et al. |
| 5,520,653 | A | 5/1996 | Reilly et al. |
| 5,573,129 | A | 11/1996 | Nagata et al. |
| 5,578,005 | A | 11/1996 | Sancoff et al. |
| 5,584,413 | A | 12/1996 | Jung |
| 5,592,948 | A | 1/1997 | Gatten |
| 5,609,580 | A | 3/1997 | Kwiatkowski et al. |
| 5,615,791 | A | 4/1997 | Vatelot et al. |
| 5,638,995 | A | 6/1997 | Mazda |
| 5,651,776 | A | 7/1997 | Appling et al. |
| 5,683,369 | A | 11/1997 | Tsukada |
| 5,725,500 | A | 3/1998 | Micheler |
| 5,758,789 | A | 6/1998 | Shin et al. |
| 5,794,107 | A | 8/1998 | Russell |
| 5,827,233 | A | 10/1998 | Futagawa et al. |
| 5,836,922 | A | 11/1998 | Hansen et al. |
| 5,873,861 | A | 2/1999 | Hitchins et al. |
| 5,893,843 | A | 4/1999 | Rodrigues Claro |
| 5,899,889 | A | 5/1999 | Futagawa et al. |
| 5,935,105 | A | 8/1999 | Manning et al. |
| 5,957,898 | A | 9/1999 | Jepson et al. |
| RE36,377 | E | 11/1999 | Gilbert |
| 5,976,112 | A | 11/1999 | Lyza, Jr. |
| 5,979,326 | A | 11/1999 | Ohinata |
| 5,980,489 | A | 11/1999 | Kriesel |
| 5,984,378 | A | 11/1999 | Ostrander et al. |
| 6,054,194 | A | 4/2000 | Kane |
| 6,056,724 | A | 5/2000 | Lacroix |
| 6,062,437 | A | 5/2000 | Mascitelli |
| 6,063,058 | A | 5/2000 | Sakamoto |
| 6,077,252 | A | 6/2000 | Siegel |
| 6,105,815 | A | 8/2000 | Mazda |
| 6,132,396 | A | 10/2000 | Antanavich et al. |
| 6,142,976 | A | 11/2000 | Kubo |
| 6,159,183 | A | 12/2000 | Neer et al. |
| 6,216,915 | B1 | 4/2001 | Harman et al. |
| 6,224,577 | B1 | 5/2001 | Dedola et al. |
| 6,250,505 | B1 | 6/2001 | Petit |
| 6,270,482 | B1 | 8/2001 | Rosoff et al. |
| 6,306,191 | B1 | 10/2001 | McInerney et al. |
| 6,315,761 | B1 | 11/2001 | Shcherbina et al. |
| 6,319,235 | B1 | 11/2001 | Yoshino |
| 6,322,535 | B1 | 11/2001 | Hitchins et al. |
| 6,322,542 | B1 | 11/2001 | Nilson et al. |
| 6,328,715 | B1 | 12/2001 | Dragan et al. |
| 6,332,876 | B1 | 12/2001 | Poynter et al. |
| 6,442,418 | B1 | 8/2002 | Evans, III et al. |
| 6,450,993 | B1 | 9/2002 | Lin |
| 6,465,024 | B1 | 10/2002 | Di et al. |
| 6,485,471 | B1 | 11/2002 | Zivitz et al. |
| 6,497,684 | B2 | 12/2002 | Witowski et al. |
| 6,558,358 | B2 | 5/2003 | Rosoff et al. |
| 6,575,930 | B1 | 6/2003 | Trombley, III et al. |
| 6,578,738 | B1 | 6/2003 | Keller |
| 6,616,000 | B1 | 9/2003 | Renz |
| 6,620,134 | B1 | 9/2003 | Trombley, III et al. |
| 6,634,524 | B1 | 10/2003 | Helmenstein |
| 6,643,537 | B1 | 11/2003 | Zatezalo et al. |
| 6,652,489 | B2 | 11/2003 | Trocki et al. |
| 6,702,143 | B2 | 3/2004 | Wang |
| 6,716,195 | B2 | 4/2004 | Nolan, Jr. et al. |
| 6,723,074 | B1 | 4/2004 | Halseth |
| 6,726,657 | B1 | 4/2004 | Dedig et al. |
| 6,731,971 | B2 | 5/2004 | Evans et al. |
| 6,773,417 | B2 | 8/2004 | Fitzgibbons et al. |
| 6,840,164 | B2 | 1/2005 | Eastman |
| 6,855,130 | B2 | 2/2005 | Saulenas et al. |
| 6,866,039 | B1 | 3/2005 | Wright et al. |
| 6,866,654 | B2 | 3/2005 | Callan et al. |
| 6,869,419 | B2 | 3/2005 | Dragan et al. |
| 6,921,384 | B2 | 7/2005 | Reilly et al. |
| RE38,770 | E | 8/2005 | Gilbert |
| 6,974,443 | B2 | 12/2005 | Reilly et al. |
| 6,984,222 | B1 | 1/2006 | Hitchins et al. |
| 7,004,213 | B2 | 2/2006 | Hansen |
| 7,011,650 | B2 | 3/2006 | Rosoff et al. |
| 7,094,216 | B2 | 8/2006 | Trombley, III et al. |
| 7,101,352 | B2 | 9/2006 | Dochon et al. |
| 7,192,416 | B1 | 3/2007 | Azzaro et al. |
| 7,192,549 | B2 | 3/2007 | Hansen |
| 7,240,926 | B2 | 7/2007 | Dalle et al. |
| 7,250,039 | B2 | 7/2007 | Fitzgerald |
| 7,309,463 | B2 | 12/2007 | Hansen |
| 7,351,221 | B2 | 4/2008 | Trombley, III et al. |
| 7,419,478 | B1 | 9/2008 | Reilly et al. |
| 7,427,281 | B2 | 9/2008 | Uber et al. |
| 7,457,804 | B2 | 11/2008 | Uber, III et al. |
| 7,462,166 | B2 | 12/2008 | Kowan et al. |
| 7,497,843 | B1 | 3/2009 | Castillo et al. |
| 7,513,378 | B2 | 4/2009 | Mori et al. |
| 7,540,856 | B2 | 6/2009 | Hitchins et al. |
| 7,553,294 | B2 | 6/2009 | Lazzaro et al. |
| 7,556,619 | B2 | 7/2009 | Spohn et al. |
| 7,563,249 | B2 | 7/2009 | Schriver et al. |
| 7,581,559 | B2 | 9/2009 | Bausmith et al. |
| 7,597,683 | B2 | 10/2009 | Myhrberg et al. |
| 7,604,623 | B2 | 10/2009 | Brunner et al. |
| 7,611,503 | B2 | 11/2009 | Spohn et al. |
| 7,621,395 | B2 | 11/2009 | Mogensen et al. |
| 7,666,169 | B2 | 2/2010 | Cowan et al. |
| 7,686,788 | B2 | 3/2010 | Freyman et al. |
| 7,766,883 | B2 | 8/2010 | Rellly et al. |
| 7,802,691 | B2 | 9/2010 | Musalek et al. |
| 7,818,992 | B2 | 10/2010 | Riley et al. |
| 7,861,893 | B2 | 1/2011 | Voegele et al. |
| 7,996,381 | B2 | 8/2011 | Uber, III et al. |
| 8,057,406 | B2 | 11/2011 | Mohiuddin |
| 8,147,464 | B2 | 4/2012 | Spohn et al. |
| 8,162,903 | B2 | 4/2012 | Reilly et al. |
| 8,337,456 | B2 | 12/2012 | Schriver et al. |
| 8,388,580 | B2 | 3/2013 | Schriver et al. |
| 8,419,676 | B2 | 4/2013 | Evans et al. |
| 8,439,863 | B2 | 5/2013 | Fago et al. |
| 8,521,716 | B2 | 8/2013 | Uber, III et al. |
| 8,540,698 | B2 | 9/2013 | Spohn et al. |
| 8,740,877 | B2 | 6/2014 | Borlaug et al. |
| 8,795,240 | B2 | 8/2014 | Chelak |
| 8,872,708 | B2 | 10/2014 | Hill et al. |
| 8,882,702 | B2 | 11/2014 | Suchecki et al. |
| 8,882,708 | B2 | 11/2014 | Hieb et al. |
| 8,919,384 | B2 | 12/2014 | Spohn et al. |
| 8,945,051 | B2 | 2/2015 | Schriver et al. |
| 8,992,489 | B2 | 3/2015 | Spohn et al. |
| 9,173,995 | B1 | 11/2015 | Tucker et al. |
| 9,180,252 | B2 | 11/2015 | Gelblum et al. |
| 9,180,260 | B2 | 11/2015 | Huang et al. |
| 9,199,033 | B1 | 12/2015 | Cowan et al. |
| 9,474,857 | B2 | 10/2016 | Riley et al. |
| 9,498,570 | B2 | 11/2016 | Cowan et al. |
| 9,555,379 | B2 | 1/2017 | Schriver et al. |
| 9,566,381 | B2 | 2/2017 | Barron et al. |
| 9,901,671 | B2 | 2/2018 | Toews et al. |
| 10,022,493 | B2 | 7/2018 | Shearer, Jr. et al. |
| 10,046,106 | B2 | 8/2018 | Cowan et al. |
| 10,105,491 | B2 | 10/2018 | Gelblum et al. |
| 10,124,110 | B2 | 11/2018 | Dedig et al. |
| 10,201,666 | B2 | 2/2019 | Cowan et al. |
| 10,398,353 | B2 | 9/2019 | Addison et al. |
| 10,420,902 | B2 | 9/2019 | Cowan et al. |
| 10,507,319 | B2 | 12/2019 | Haury et al. |
| 10,549,084 | B2 | 2/2020 | Sokolov et al. |
| 10,857,345 | B2 | 12/2020 | Uber, III et al. |
| 10,933,190 | B2 | 3/2021 | Berry et al. |
| 11,083,882 | B2 | 8/2021 | Schrauder et al. |
| 11,207,462 | B2 | 12/2021 | Cowan et al. |
| 11,389,585 | B2 | 7/2022 | Spohn et al. |

(56) References Cited

U.S. PATENT DOCUMENTS

| | | | |
|---|---|---|---|
| 11,413,403 B2 | 8/2022 | Yoshioka et al. | |
| 11,547,793 B2 | 1/2023 | Cowan et al. | |
| 2001/0004466 A1 | 6/2001 | Heinz et al. | |
| 2001/0018575 A1 | 8/2001 | Lyza | |
| 2002/0010596 A1 | 1/2002 | Matory | |
| 2002/0147429 A1 | 10/2002 | Cowan et al. | |
| 2003/0216695 A1 | 11/2003 | Yang | |
| 2003/0226539 A1 | 12/2003 | Kim et al. | |
| 2004/0068224 A1 | 4/2004 | Couvillon et al. | |
| 2004/0092905 A1 | 5/2004 | Azzolini | |
| 2004/0116893 A1 | 6/2004 | Spohn et al. | |
| 2004/0154788 A1 | 8/2004 | Symonds | |
| 2004/0186457 A1 | 9/2004 | Truitt et al. | |
| 2004/0249344 A1 | 12/2004 | Nemoto et al. | |
| 2004/0254541 A1 | 12/2004 | Wong et al. | |
| 2005/0082828 A1 | 4/2005 | Wicks et al. | |
| 2005/0121103 A1 | 6/2005 | Steigerwalt et al. | |
| 2006/0052794 A1 | 3/2006 | Mcgill et al. | |
| 2006/0149213 A1 | 7/2006 | Raybuck | |
| 2007/0068964 A1 | 3/2007 | Tanaami et al. | |
| 2007/0129705 A1 | 6/2007 | Trombley et al. | |
| 2008/0045925 A1 | 2/2008 | Stepovich et al. | |
| 2008/0146996 A1 | 6/2008 | Smisson et al. | |
| 2009/0069792 A1 | 3/2009 | Frey et al. | |
| 2009/0112087 A1 | 4/2009 | Fago | |
| 2009/0216192 A1 | 8/2009 | Schriver et al. | |
| 2009/0218243 A1 | 9/2009 | Gyrn et al. | |
| 2010/0063445 A1 | 3/2010 | Sternberg et al. | |
| 2010/0089475 A1 | 4/2010 | Tracey | |
| 2010/0091361 A1 | 4/2010 | Yuuki | |
| 2010/0114064 A1 | 5/2010 | Kalafut et al. | |
| 2010/0286650 A1 | 11/2010 | Fitzgerald | |
| 2011/0009826 A1 | 1/2011 | Lewis | |
| 2011/0218434 A1 | 9/2011 | Ziemba et al. | |
| 2011/0275988 A1 | 11/2011 | Davis et al. | |
| 2011/0282196 A1 | 11/2011 | Martz | |
| 2012/0020911 A1 | 1/2012 | Seliktar et al. | |
| 2012/0101472 A1 | 4/2012 | Schroeder et al. | |
| 2012/0123257 A1* | 5/2012 | Stokes, Jr. .......... | A61M 5/1407 600/432 |
| 2012/0178629 A1 | 7/2012 | Hudson et al. | |
| 2012/0217231 A1 | 8/2012 | Moore et al. | |
| 2012/0245560 A1 | 9/2012 | Hochman | |
| 2012/0253291 A1 | 10/2012 | Ivosevic et al. | |
| 2013/0023048 A1 | 1/2013 | Kim et al. | |
| 2013/0030291 A1 | 1/2013 | Lewis | |
| 2013/0043273 A1 | 2/2013 | Lee et al. | |
| 2013/0053774 A1 | 2/2013 | Kirkpatrick | |
| 2013/0067416 A1 | 3/2013 | Barron et al. | |
| 2013/0204130 A1 | 8/2013 | McArthur et al. | |
| 2013/0211248 A1 | 8/2013 | Cowan et al. | |
| 2013/0310756 A1 | 11/2013 | Whalley et al. | |
| 2014/0124087 A1 | 5/2014 | Anderson et al. | |
| 2014/0261713 A1 | 9/2014 | Schriver et al. | |
| 2014/0276652 A1 | 9/2014 | Gittard | |
| 2014/0374353 A1 | 12/2014 | Wright et al. | |
| 2015/0260325 A1 | 9/2015 | Quick | |
| 2016/0030662 A1 | 2/2016 | Uber, III et al. | |
| 2016/0250409 A1 | 9/2016 | Dedig et al. | |
| 2016/0287809 A1* | 10/2016 | Sharma ............ | A61M 25/0108 |
| 2017/0035974 A1 | 2/2017 | Berry et al. | |
| 2017/0100534 A1 | 4/2017 | Fukikoshi et al. | |
| 2017/0165427 A1 | 6/2017 | Uber, III et al. | |
| 2017/0232173 A1 | 8/2017 | Perry et al. | |
| 2018/0161496 A1 | 6/2018 | Berry et al. | |
| 2018/0280630 A1 | 10/2018 | Jiang et al. | |
| 2018/0296755 A1 | 10/2018 | Dahlin et al. | |
| 2019/0240424 A1 | 8/2019 | Yoshioka et al. | |
| 2020/0164141 A1 | 5/2020 | Biermann et al. | |
| 2020/0206490 A1 | 7/2020 | Bae | |
| 2020/0246541 A1 | 8/2020 | Neftel et al. | |
| 2021/0023298 A1 | 1/2021 | McDermott et al. | |
| 2021/0146064 A1 | 5/2021 | Knutsson | |
| 2021/0193289 A1 | 6/2021 | Cowan et al. | |
| 2021/0220561 A1 | 7/2021 | Spohn et al. | |
| 2021/0316065 A1 | 10/2021 | Berry et al. | |
| 2021/0353870 A1 | 11/2021 | Volkar et al. | |
| 2023/0181816 A1 | 6/2023 | Lee | |

FOREIGN PATENT DOCUMENTS

| | | | |
|---|---|---|---|
| EP | 0446898 A2 | | 9/1991 |
| EP | 1086661 A2 | | 3/2001 |
| EP | 1572266 A2 | | 9/2005 |
| EP | 1769849 A1 | | 4/2007 |
| EP | 1800704 A1 | | 6/2007 |
| EP | 2005934 A2 | | 12/2008 |
| EP | 2098258 A1 | | 9/2009 |
| EP | 2692375 A1 | | 2/2014 |
| EP | 2719420 A1 | | 4/2014 |
| EP | 2754459 A1 | | 7/2014 |
| EP | 2767299 A1 | | 8/2014 |
| EP | 3057648 A1 | | 8/2016 |
| EP | 2962770 B1 | | 3/2017 |
| EP | 3248635 A1 | | 11/2017 |
| FR | 1288915 A | | 3/1962 |
| FR | 78023 E | * | 5/1962 |
| GB | 2214819 A | | 9/1989 |
| GB | 2374143 A | | 10/2002 |
| JP | H02-88664 | | 7/1990 |
| JP | H0849598 A | | 2/1996 |
| JP | H10999034 A | | 4/1997 |
| JP | 5485885 B2 | | 5/2014 |
| JP | 5511409 B2 | | 6/2014 |
| JP | 5882595 B2 | | 3/2016 |
| JP | 5897798 B2 | | 3/2016 |
| JP | 6552258 B2 | | 7/2019 |
| JP | 6839853 B2 | | 3/2021 |
| WO | 9221391 A1 | | 12/1992 |
| WO | 9528195 A1 | | 10/1995 |
| WO | 9707841 A2 | | 3/1997 |
| WO | 0204049 A1 | | 1/2002 |
| WO | 02066100 A2 | | 8/2002 |
| WO | 2004033023 A1 | | 4/2004 |
| WO | 2005035995 A1 | | 4/2005 |
| WO | 2007133942 A2 | | 11/2007 |
| WO | 2008050218 A2 | | 5/2008 |
| WO | 2008153831 A2 | | 12/2008 |
| WO | 2009038955 A1 | | 3/2009 |
| WO | 2010004206 A2 | | 1/2010 |
| WO | 2010014654 A1 | | 2/2010 |
| WO | 2011011346 A1 | | 1/2011 |
| WO | 2011125303 A1 | | 10/2011 |
| WO | 2011129175 A1 | | 10/2011 |
| WO | 2012061140 A1 | | 5/2012 |
| WO | 2012155035 A1 | | 11/2012 |
| WO | 2013043868 A1 | | 3/2013 |
| WO | 2013043881 A1 | | 3/2013 |
| WO | 2013043889 A1 | | 3/2013 |
| WO | 2014027009 A1 | | 2/2014 |
| WO | 2014055283 A1 | | 4/2014 |
| WO | 2014160326 A1 | | 10/2014 |
| WO | 2015058088 A1 | | 4/2015 |
| WO | 2015066506 A2 | | 5/2015 |
| WO | 2015164783 A1 | | 10/2015 |
| WO | 2016058946 A1 | | 4/2016 |
| WO | 2016069711 A1 | | 5/2016 |
| WO | 2016069714 A1 | | 5/2016 |
| WO | 2016112163 A1 | | 7/2016 |
| WO | 2016157886 A1 | | 10/2016 |
| WO | 2016172467 A1 | | 10/2016 |
| WO | 2016190904 A1 | | 12/2016 |
| WO | 2016191485 A1 | | 12/2016 |
| WO | 2017040154 A1 | | 3/2017 |
| WO | 2017091635 A1 | | 6/2017 |
| WO | 2017091636 A1 | | 6/2017 |
| WO | 2017091643 A1 | | 6/2017 |
| WO | 2018053074 A1 | | 3/2018 |
| WO | 2018057386 A1 | | 3/2018 |
| WO | 2018218132 A1 | | 11/2018 |
| WO | 2019046259 A1 | | 3/2019 |
| WO | 2019046260 A1 | | 3/2019 |
| WO | 2019046299 A1 | | 3/2019 |
| WO | 2019152978 A1 | | 8/2019 |

(56) References Cited

FOREIGN PATENT DOCUMENTS

| | | | |
|---|---|---|---|
| WO | 2019204605 | A1 | 10/2019 |
| WO | 2019204617 | A1 | 10/2019 |
| WO | 2020055785 | A1 | 3/2020 |
| WO | 2020055818 | A1 | 3/2020 |
| WO | 2021050507 | A1 | 3/2021 |
| WO | 2021168076 | A1 | 8/2021 |
| WO | 2021173743 | A1 | 9/2021 |
| WO | 2021188416 | A1 | 9/2021 |
| WO | 2021188460 | A1 | 9/2021 |
| WO | 2021222619 | A1 | 11/2021 |
| WO | 2021247595 | A1 | 12/2021 |
| WO | 2021257667 | A1 | 12/2021 |
| WO | 2021257699 | A1 | 12/2021 |
| WO | 2022035791 | A1 | 2/2022 |
| WO | 2022036058 | A1 | 2/2022 |
| WO | 2022265695 | A1 | 12/2022 |

OTHER PUBLICATIONS

UN; Haluk, "A New Device Preventing Air Embolism During the Angiography, Air Trap Device: An In-Vitro Experimental Air Emboli Study", Proceedings of the 2019 Design of Medical Devices Conference, 2019.

* cited by examiner

FLUID PATHS FOR ANGIOGRAPHY INJECTOR ASSEMBLY

CROSS-REFERENCE TO RELATED APPLICATIONS

This application is a U.S. national phase application under 35 U.S.C. § 371 of PCT International Application No. PCT/US2021/022321, filed Mar. 15, 2021, and claims the benefit of U.S. Provisional Patent Application No. 62/990,141 filed on Mar. 16, 2020 and U.S. Provisional Patent Application No. 62/990,179 filed on Mar. 16, 2020, the disclosures of which are hereby incorporated by reference in their entireties.

BACKGROUND OF THE DISCLOSURE

Field of the Disclosure

The present disclosure relates generally to fluid injector systems and associated fluid path assemblies for high pressure injection of medical fluids. More specifically, the present disclosure describes a fluid delivery system and fluid path assembly having a downstream automated shutoff valve and an upstream air detector to minimize the chance of air being delivered to a patient during an injection procedure.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent (such as saline or Ringer's lactate), and other medical fluids, have been developed for use in procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate. In certain applications, such as angiography, the medical fluids may be injected directly into the cardiac system at fluid pressures up to 1200 psi.

During certain injection procedures at these high fluid pressures with fluid being administered directly to the cardiac system, it is imperative that no air or other gas bubble be co-injected with the medical fluid as patient harm may result. For angiography, injection of even small volumes of air during an injection procedure may be harmful and must be avoided. The danger associated with air injection during angiography procedures is enhanced since the fluids are injected directly into the cardiac system. Further, at pressures of up to 1200 psi, the speed at which the fluid (and inadvertent air bubbles) flow through the fluid path and the compressibility of gas relative to liquids compresses the volume of air bubbles in the fluid line compared to the same molar amount of air at lower pressures make stopping of an air bubble after detection and before injection into the patient a challenge. For example, once the highly compressed air leaves the injector system and enters the patient vasculature system which is at significantly lower pressures (e.g., approximately 1 atm), the volume of the air bubble may increase significantly due to the reduced pressure. Thus, injection of even small volumes of air at the high pressures used for CV procedures must be strenuously avoided. Additionally, because of the high pressures used, the speed of the fluid flowing through the fluid path, the air compressibility, and/or the volume compliance of the system and its components, air may potentially still be injected into the patient even if actuation of the syringe piston is halted.

SUMMARY OF THE DISCLOSURE

In view of the foregoing, there exists a need for devices, systems, and methods for preventing air from being delivered to a patient during an injection procedure. Embodiments of the present disclosure are directed to a fluid injector system including at least one syringe configured for injecting medical fluid and a fluid path assembly in fluid communication with the at least one syringe, the fluid path assembly including at least one air detection region. The fluid injector system further includes an air detector configured to detect one or more air bubbles in a fluid path associated with the air detection region, at least one shutoff valve at a distal end of the fluid path assembly, and at least one processor programmed or configured to actuate the at least one shutoff valve in response to the air detector detecting the one or more air bubbles in the fluid path associated with the air detection region to prevent fluid flow out of the fluid path assembly. The fluid path assembly has a length greater than a distance that an air bubble can travel or expand during an actuation time of the at least one shutoff valve.

In some embodiments, the actuation time of the at least one shutoff valve is a time interval between a time at which the air bubble is detected in the air detection region and a time at which the at least one shutoff valve reaches a stop position.

In some embodiments, the fluid path assembly includes a fluid path length having a path length of between approximately 1000 millimeters and approximately 1400 millimeters.

In some embodiments, the fluid injector system further includes a fluid path tubing element including a plurality of tubes arranged in a zig-zag configuration and connected to one another in series. In some embodiments, the plurality of tubes are parallel to one another.

In some embodiments, the plurality of tubes are connected to one another by a plurality of associated u-turn elements. In some embodiments, each of the plurality of associated u-turn elements defines a 180° turn to divert fluid flow from one of the plurality of tubes to another of the plurality of tubes. In some embodiments, the plurality of u-turn elements are formed in a pair of end caps, and the pair of end caps are joined to open ends of the plurality of tubes to form a fluid path between an inlet port and an outlet port.

In some embodiments, the air detection region is associated with the inlet port of the fluid path tubing element.

In some embodiments, a total fluid path length of the fluid path tubing element is between approximately 1000 millimeters and approximately 1400 millimeters.

In some embodiments, the fluid injector system further includes a fluid path tubing element including a tortuous path.

In some embodiments, the fluid path tubing element includes a housing having a plurality of baffles to disrupt laminar flow of fluid through the housing.

In some embodiments, the housing includes a widened portion having an increased cross-sectional area configured to create a fluid pressure drop within the widened portion.

In some embodiments, the plurality of baffles extend across a centerline of the housing such that fluid is forced to flow around the plurality of baffles.

In some embodiments, the plurality of baffles includes at least one baffle extending from a first inner surface into a fluid path of the housing, and at least one baffle extending from a second inner surface into the fluid path of the housing and opposite of the first inner surface. The at least one baffle extending from the second inner surface of the housing is offset in a longitudinal direction from the at least one baffle extending from the first inner surface of the housing. In some embodiments, the plurality of baffles are angled to include a plurality of corners.

In some embodiments, the fluid path tubing element is movable between a priming position and an injection position. In the priming position, an outlet of the fluid path tubing element is oriented substantially upward such that air bubbles within the fluid path flow towards the outlet due, at least in part, to buoyancy. In the injection position, the outlet of the fluid path tubing element is oriented downward such that air bubbles within the fluid path flow away from the outlet due, at least in part, to buoyancy.

In some embodiments, the at least one processor is programmed or configured to move the fluid path tubing element between the priming position and the injection position.

Other embodiments of the present disclosure are directed to a fluid path tubing element for a fluid injector system. The fluid path tubing element includes an inlet port configured for fluid communication with at least one syringe, an outlet port configured for fluid communication with a valve, a tubing portion having a plurality of individual parallel tubes, and a plurality of u-turn elements connecting the plurality of individual parallel tubes in series in a zig-zag configuration. In some embodiments, each of the plurality of associated u-turn elements defines a 180° turn to divert fluid flow from one of the plurality of tubes to another of the plurality of tubes.

In some embodiments, the plurality of u-turn elements are formed in a pair of end caps, and the pair of end caps are joined to open ends of the plurality of individual parallel tubes of the tubing portion to form a fluid path between the inlet port and the outlet port.

In some embodiments, the total length of the fluid path tubing element is greater than a distance that an air bubble can travel or expand during an actuation time of the valve.

In some embodiments, the inlet port includes an air detection region configured for operative communication with an air detector configured to detect one or more air bubbles in the air detection region.

In some embodiments, a total fluid path length of the fluid path tubing element is between approximately 1000 millimeters and approximately 1400 millimeters.

Other embodiments of the present disclosure are directed to a fluid path tubing element for a fluid injector system. The fluid path tubing element includes a housing having an inlet port configured for fluid communication with at least one fluid injector and an outlet port configured for fluid communication with a valve, and a plurality of baffles to disrupt laminar flow of fluid through the housing. The plurality of baffles extend across a centerline of the housing such that fluid is forced to flow around the plurality of baffles.

In some embodiments, the housing includes a widened portion having an increased cross-sectional area configured to create a fluid pressure drop within the widened portion.

In some embodiments, the plurality of baffles includes at least one baffle extending from a first inner surface into a fluid path of the housing, and at least one baffle extending from a second inner surface into the housing of the housing and opposite the first inner surface. The at least one baffle extending from the second inner surface of the housing is offset in a longitudinal direction from the at least one baffle extending from the first inner surface of the housing. In some embodiments, the plurality of baffles are angled to include a plurality of corners. In some embodiments, the plurality of baffles are directional.

In some embodiments, the inlet port includes an air detection region configured for operative communication with an air detector configured to detect one or more air bubbles in the air detection region.

In some embodiments, a total fluid path length of the fluid path tubing element is between approximately 1000 millimeters and approximately 1400 millimeters.

Further aspects or examples of the present disclosure are described in the following numbered clauses:

Clause 1. A fluid injector system comprising: at least one syringe configured for injecting medical fluid; a fluid path assembly in fluid communication with the at least one syringe, the fluid path assembly comprising at least one air detection region; an air detector configured to detect one or more air bubbles in a fluid path associated with the air detection region; at least one shutoff valve at a distal end of the fluid path assembly; and at least one processor programmed or configured to actuate the at least one shutoff valve in response to the air detector detecting the one or more air bubbles in the fluid path associated with the air detection region to prevent fluid flow out of the fluid path assembly, wherein the fluid path assembly has a length greater than a distance that an air bubble can travel or expand during an actuation time of the at least one shutoff valve.

Clause 2. The fluid injector system of clause 1, wherein the actuation time of the at least one shutoff valve is a time interval between a time at which the air bubble is detected in the air detection region and a time at which the at least one shutoff valve reaches a stop position.

Clause 3. The fluid injector system of clause 1 or 2, wherein the fluid path assembly comprises a fluid path length having a path length of between approximately 1000 millimeters and approximately 1400 millimeters.

Clause 4. The fluid injector system of any of clauses 1 to 3, further comprising a fluid path tubing element comprising a plurality of tubes arranged in a zig-zag configuration and connected to one another in series.

Clause 5. The fluid injector system of any of clauses 1 to 4, wherein the plurality of tubes are parallel to one another.

Clause 6. The fluid injector system of any of clauses 1 to 5, wherein the plurality of tubes are connected to one another by a plurality of associated u-turn elements.

Clause 7. The fluid injector system of any of clauses 1 to 6, wherein each of the plurality of associated u-turn elements defines a 180° turn to divert fluid flow from one of the plurality of tubes to another of the plurality of tubes.

Clause 8. The fluid injector system of any of clauses 1 to 7, wherein the plurality of u-turn elements are formed in a pair of end caps, and wherein the pair of end caps are joined to open ends of the plurality of tubes to form a fluid path between an inlet port and an outlet port.

Clause 9. The fluid injector system of any of clauses 1 to 8, wherein the air detection region is associated with the inlet port of the fluid path tubing element.

Clause 10. The fluid injector system of any of clauses 1 to 9, wherein a total fluid path length of the fluid path tubing element is between approximately 1000 millimeters and approximately 1400 millimeters.

Clause 11. The fluid injector system of any of clauses 1 to 10, further comprising a fluid path tubing element comprising a tortuous path.

Clause 12. The fluid injector system of any of clauses 1 to 11, wherein the fluid path tubing element comprises a housing having a plurality of baffles to disrupt laminar flow of fluid through the housing.

Clause 13. The fluid injector system of any of clauses 1 to 12, wherein the housing comprises a widened portion having an increased cross-sectional area configured to create a fluid pressure drop within the widened portion.

Clause 14. The fluid injector system of any of clauses 1 to 13, wherein the plurality of baffles extend across a centerline of the housing such that fluid is forced to flow around the plurality of baffles.

Clause 15. The fluid injector system of any of clauses 1 to 14, wherein the plurality of baffles comprises: at least one baffle extending from a first inner surface into a fluid path of the housing; and at least one baffle extending from a second inner surface into the fluid path of the housing and opposite of the first inner surface, wherein the at least one baffle extending from the second inner surface of the housing is offset in a longitudinal direction from the at least one baffle extending from the first inner surface of the housing.

Clause 16. The fluid injector system of any of clauses 1 to 15, wherein the plurality of baffles are angled to include a plurality of corners.

Clause 17. The fluid injector system of any of clauses 1 to 16, wherein the fluid path tubing element is movable between a priming position and an injection position, wherein, in the priming position, an outlet of the fluid path tubing element is oriented substantially upward such that air bubbles within the fluid path flow towards the outlet due, at least in part, to buoyancy, and wherein, in the injection position, the outlet of the fluid path tubing element is oriented downward such that air bubbles within the fluid path flow away from the outlet due, at least in part, to buoyancy.

Clause 18. The fluid injector system of any of clauses 1 to 17, wherein the at least one processor is programmed or configured to move the fluid path tubing element between the priming position and the injection position.

Clause 19. A fluid path tubing element for a fluid injector system, the fluid path tubing element comprising: an inlet port configured for fluid communication with at least one syringe; an outlet port configured for fluid communication with a valve; a tubing portion having a plurality of individual parallel tubes; and a plurality of u-turn elements connecting the plurality of individual parallel tubes in series in a zig-zag configuration.

Clause 20. The fluid injector system of clause 19, wherein each of the plurality of associated u-turn elements defines a 180° turn to divert fluid flow from one of the plurality of tubes to another of the plurality of tubes.

Clause 21. The fluid path tubing element of clause 19 or 20, wherein the plurality of u-turn elements are formed in a pair of end caps, and wherein the pair of end caps are joined to open ends of the plurality of individual parallel tubes of the tubing portion to form a fluid path between the inlet port and the outlet port.

Clause 22. The fluid path tubing element of any of clauses 19 to 21, wherein the total length of the fluid path tubing element is greater than a distance that an air bubble can travel or expand during an actuation time of the valve.

Clause 23. The fluid path tubing element of any of clauses 19 to 22, wherein the inlet port comprises an air detection region configured for operative communication with an air detector configured to detect one or more air bubbles in the air detection region.

Clause 24. The fluid path tubing element of any of clauses 19 to 23, wherein a total fluid path length of the fluid path tubing element is between approximately 1000 millimeters and approximately 1400 millimeters.

Clause 25. A fluid path tubing element for a fluid injector system, the fluid path tubing element comprising: a housing having an inlet port configured for fluid communication with at least one fluid injector and an outlet port configured for fluid communication with a valve; and a plurality of baffles to disrupt laminar flow of fluid through the housing, wherein the plurality of baffles extend across a centerline of the housing such that fluid is forced to flow around the plurality of baffles.

Clause 26. The fluid path tubing element of clause 25, wherein the housing comprises a widened portion having an increased cross-sectional area configured to create a fluid pressure drop within the widened portion.

Clause 27. The fluid path tubing element of clause 25 or 26, wherein the plurality of baffles comprises: at least one baffle extending from a first inner surface into a fluid path of the housing; and at least one baffle extending from the second inner surface into the housing of the housing and opposite the first inner surface, wherein the at least one baffle extending from the second inner surface of the housing is offset in a longitudinal direction from the at least one baffle extending from the first inner surface of the housing.

Clause 28. The fluid path tubing element of any of clauses 25 to 27, wherein the plurality of baffles are angled to include a plurality of corners.

Clause 29. The fluid path element tubing element of any of clauses 25 to 28, wherein the plurality of baffles are directional.

Clause 30. The fluid path tubing element of any of clauses 25 to 29, wherein the inlet port comprises an air detection region configured for operative communication with an air detector configured to detect one or more air bubbles in the air detection region.

Clause 31. The fluid path tubing element of any of clauses 25 to 30, wherein a total fluid path length of the fluid path tubing element is between approximately 1000 millimeters and approximately 1400 millimeters.

Further details and advantages of the various examples described in detail herein will become clear upon reviewing the following detailed description of the various examples in conjunction with the accompanying drawing figures.

DETAILED DESCRIPTION

Figure 1A:
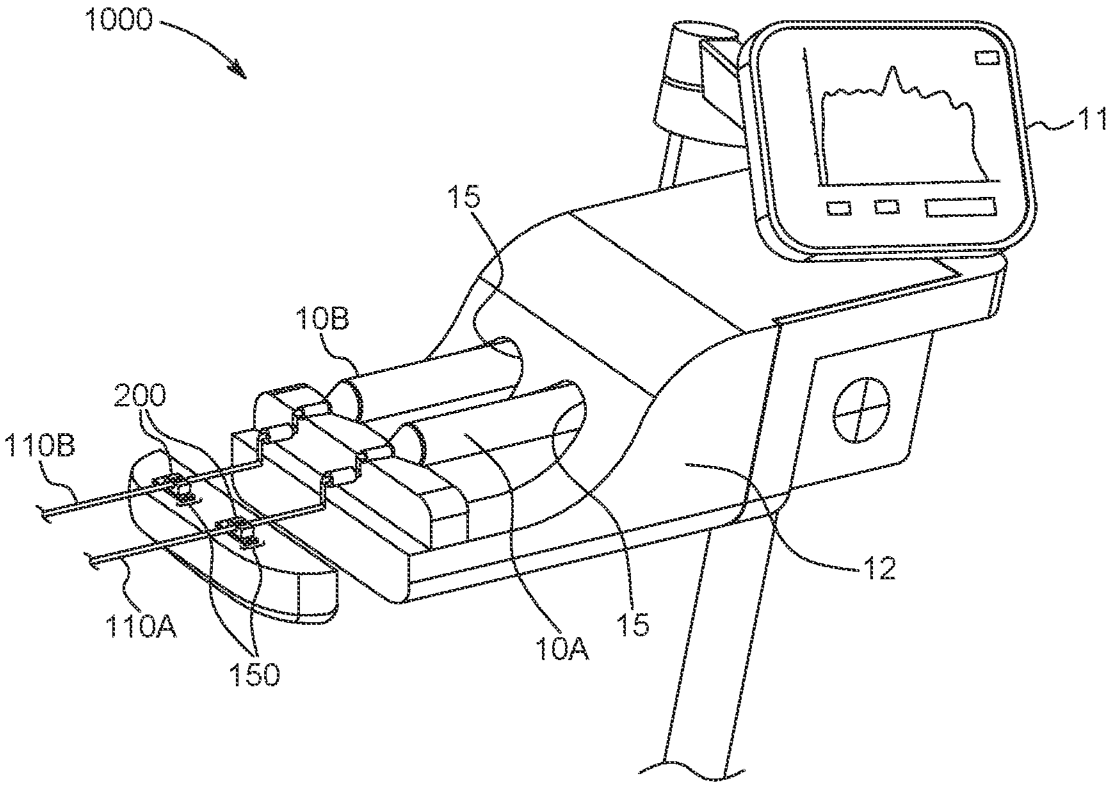
FIG. 1A is a perspective view of a fluid injector system according to an embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. Spatial or directional terms, such as "left", "right", "inner", "outer", "above", "below", and the like, are not to be considered as limiting as the invention can assume various alternative orientations.

As used herein, the singular form of "a", "an", and "the" include plural referents unless the context clearly dictates otherwise.

All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a component of a fluid delivery system such as a fluid reservoir, a syringe, or a fluid line, the term "distal" refers to a portion of said component nearest to a patient. When used in relation to a component of an injector system such as a fluid reservoir, a syringe, or a fluid line, the term "proximal" refers to a portion of said component nearest to the injector of the injector system (i.e. the portion of said component farthest from the patient). When used in relation to a component of a fluid delivery system such as a fluid reservoir, a syringe, or a fluid line, the term "upstream" refers to a direction away from the patient and towards the injector of the injector system. For example, if a first component is referred to as being "upstream" of a second component, the first component is located nearer to the injector than the second component is to the injector. When used in relation to a component of a fluid delivery system such as a fluid reservoir, a syringe, or a fluid line, the term "downstream" refers to a direction towards the patient and away from the injector of the fluid delivery system. For example, if a first component is referred to as being "downstream" of a second component, the first component is located nearer to the patient than the second component is to the patient.

As used herein, the terms "capacitance" and "impedance" are used interchangeably to refer to a volumetric expansion of injector components, such as fluid reservoirs, syringes, fluid lines, and/or other components of a fluid delivery system as a result of pressurized fluids with such components and/or uptake of mechanical slack by force applied to components. Capacitance and impedance may be due to high injection pressures, which may be on the order of 1200 psi in some angiographic procedures, and may result in a volume of fluid held within a portion of a component in excess of the desired quantity selected for the injection procedure or the resting volume of the component. Additionally, capacitance of various components can, if not properly accounted for, adversely affect the accuracy of pressure sensors of the injector system because the volumetric expansion of components can cause an artificial drop in measured pressure of those components.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to." The term "not greater than" is synonymous with "less than or equal to."

It is to be understood that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

While the systems and apparatuses described herein are with reference to an angiography (CV) injection system, other pressurized injection protocols, such as computed tomography (CT) and magnetic resonance imaging (MRI) may also incorporate the various embodiments described herein for preventing injection of air.

Referring to the drawings in which like reference characters refer to like parts throughout the several views thereof, the present disclosure is generally directed to fluid injector systems and fluid path assemblies for detecting and preventing the delivery of one or more air bubbles that may inadvertently occur during an injection procedure. Injection of air to the patient's cardiovascular system is prevented by closing the fluid path assembly and ensuring that the air has insufficient time to reach the closure point in the time required to close the fluid path assembly. The length and/or volume of the fluid path assembly, including various fluid path tubing elements thereof, may be selected based on injection and apparatus parameters to prevent fluid communication between syringes of the fluid injector and a patient tube set downstream of an automated remote shutoff valve, such injection and apparatus parameters including, for example: flow rate, fluid viscosity, ID of tubing, response time of a processor upon detection of one or more air bubbles, and time necessary for the processor to communicate to and actuate a downstream automated remote shutoff valve to a stop position.

Referring first to FIG. 1A, an embodiment of a dual syringe angiography injector system 1000 is illustrated. The angiography injector system 1000 is configured for injection of two medical fluids through a first fluid path 110A for a medical fluid, such as an imaging contrast media for an angiography injection procedure, and a second fluid path 110B for a flushing fluid, such as saline or Ringer's lactate. The dual syringe angiography injector system 1000 may include an injector housing 12 having two syringe ports 15 configured to engage two syringes 10A, 10B. In some embodiments, the syringes 10A, 10B may be retained within corresponding pressure jackets for example to prevent pressure-induced swelling and potential bursting of the syringes 10A, 10B.

The injector housing 12 may further include at least one graphical user interface (GUI) 11 through which an operator can view and control the status of an injection procedure. The GUI 11 may be in operative communication with a controller 900 (see FIG. 2) which sends and receives commands to and from the GUI 11.

The dual syringe angiography injector system 1000 may further include at least one upstream air detector 200 for detecting one or more air bubbles within an air detection tubing region 150 of the first fluid path 110A and the second fluid path 110B. The air detection tubing region 150 may for example, be associated with a proximal portion of the first fluid path 110A and the second fluid path 110B. In some embodiments, the at least one air detector 200 may be a single module having at least one sensor operatively associated with each of the first fluid path 110A and the second fluid path 110B. In some embodiments, the at least one air detector 200 may include at least two distinct modules, each module operatively associated with one of the first fluid path 110A and the second fluid path 110B. The at least one air detector 200 may be in operative communication with the controller 900 (see FIG. 2) such that the at least one air detector 200 may send and the controller 900 may receive signals from the at least one air detector 200 indicating the detection of the presence of one or more air bubbles in one or both of the first fluid path 110A and/or the second fluid path 110B. The at least one air detector 200 may include an ultrasonic sensor, and optical sensor, or the like, configured to detect the one or more air bubbles within the fluid path.

Figure 1B:
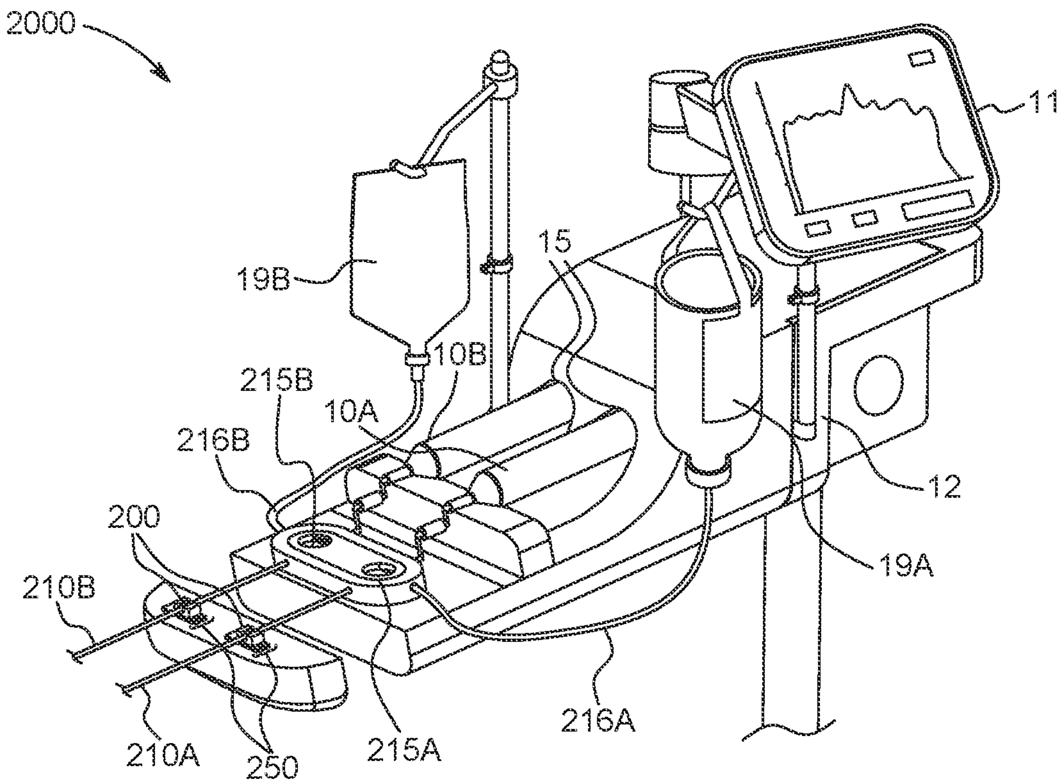
FIG. 1B is a perspective view of a fluid injector system according to an embodiment of the present disclosure.

Referring now to FIG. 1B, an embodiment of a dual syringe angiography injector system 2000 is illustrated for multi-patient use. The angiography injector system 1000 is configured for injection of two medical fluids through a first fluid path 210A for a medical fluid, such as an imaging contrast media for an angiography injection procedure, and a second fluid path 210B for a flushing fluid, such as saline or Ringer's lactate. The dual syringe angiography injector system 1000 may include an injector housing 12 having two syringe ports 15 configured to engage two syringes 10A, 10B. In some embodiments, the syringes 10A, 10B may be retained within corresponding pressure jackets, for example to prevent pressure-induced swelling and potential bursting of the syringes 10A, 10B.

The angiography injector system 2000 may further include bulk fluid containers 19A and 19B for filling and refilling the respective syringes 10A, 10B with imaging contrast media and flushing fluid, respectively, through bulk fluid paths 216A and 216B and bulk fluid valves 215A and 215B, respectively, during multiple patient fluid injection procedures.

The injector housing 12 may further include at least one graphical user interface (GUI) 11 through which an operator can view and control the status of an injection procedure. The GUI 11 may be in operative communication with a controller 900 (see FIG. 2) which sends and receives commands to and from the GUI 11.

The dual syringe angiography injector system 1000 may further include at least one air detector 200 for detecting one or air bubbles within an air detection tubing region 150 of the first fluid path 210A and the second fluid path 210B. The air detection tubing region 150 may for example, be associated with a proximal portion of the first fluid path 210A and the second fluid path 210B. In some embodiments, the at least one air detector 200 may be a single module having at least one sensor operatively associated with each of the first fluid path 210A and the second fluid path 210B. In some embodiments, the at least one air detector 200 may include at least two distinct modules, each module operatively associated with one of the first fluid path 210A and the second fluid path 210B. The at least one air detector 200 may be in operative communication with the controller 900 (FIG. 2) such that the at least one air detector 200 may send and the controller 900 may receive signals from the at least one air detector 200 indicating detection of the presence of one or more air bubbles in one or both of the first fluid path 210A and/or the second fluid path 210B. The at least one air detector 200 may include an ultrasonic sensor, and optical sensor, or the like configured to detect the one or more air bubbles within the fluid path.

Figure 2:
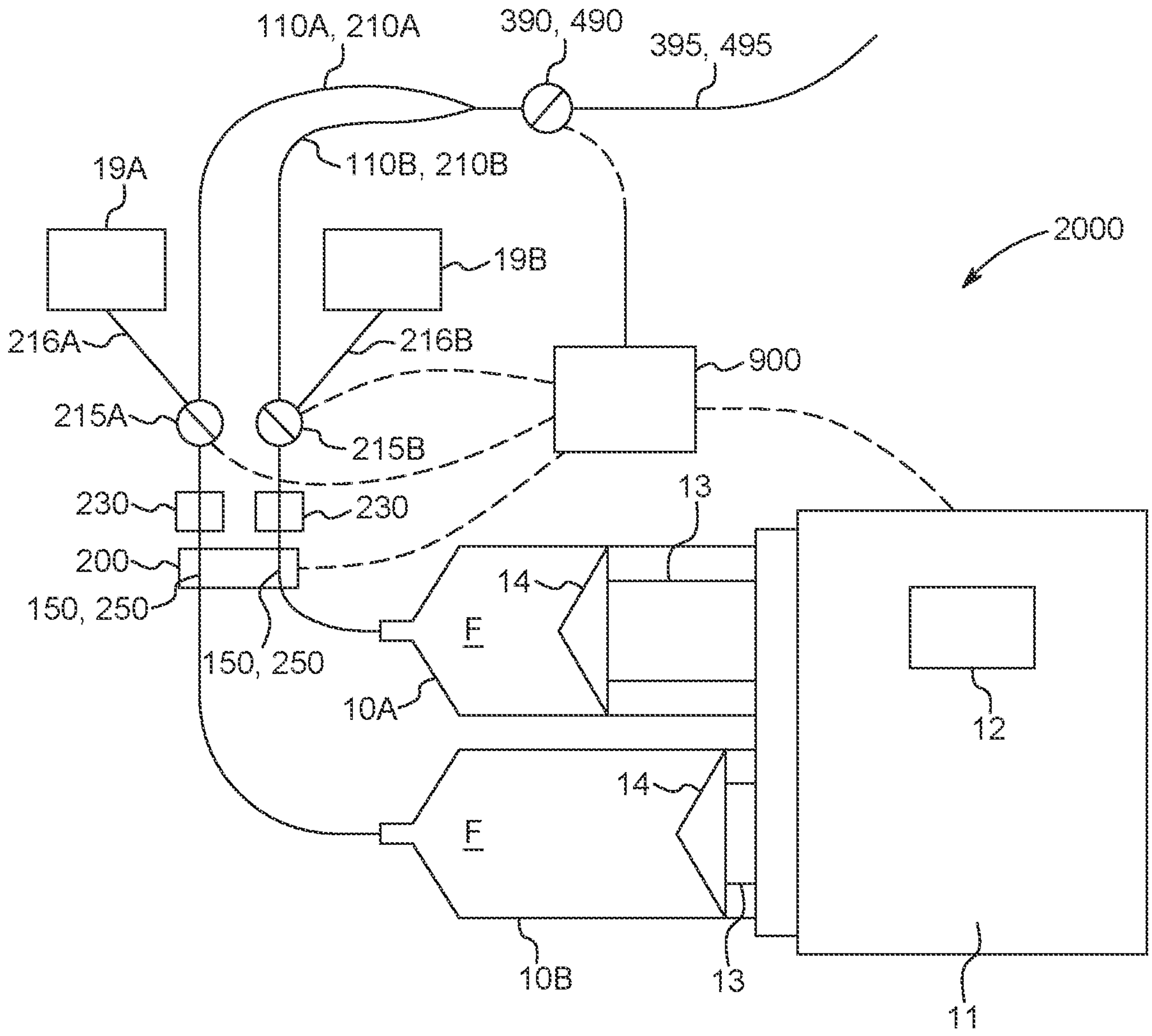
FIG. 2 is a schematic view of a fluid injector system in accordance with an embodiment of the present disclosure.

Referring to FIG. 2, a schematic diagram of the injection system 2000 shown in FIG. 1B is illustrated. The injector system 2000 includes a piston 13 associated with each of the syringes 10A, 10B that drives a plunger 14 within a barrel of each syringe 10. The controller 900 is operatively associated with the pistons 13 to reciprocatively move the plungers 14 within the syringes 10A, 10B and thereby execute an injection procedure. In particular, the controller 900 may include at least one processor programmed or configured to actuate the pistons 13 and various other components of the injector system 1000 as described herein, to take in and deliver the medical fluids according to a programmed protocol for an injection procedure. The controller 900 may include computer readable media, such as memory, on which one or more injection protocols may be stored for execution by the at least one processor.

The controller 900 may be programmed or configured to execute a filling operation during which the piston 13 associated with each syringe 10A, 10B is withdrawn toward a proximal end of the syringe 10 A, 10B to draw medical fluid F (e.g. imaging contrast media and flushing fluid) into the syringe 10A, 10B from the bulk fluid containers 19A, 19B. During such filling operation, the controller 900 may be programmed or configured to selectively actuate the bulk fluid valves 215A and 215B to establish fluid communication between the respective syringes 10A, 10B and the bulk fluid container 19A, 19B via the bulk fluid paths 216A and 216B to control filling of the syringe with the appropriate medical fluid. Upon completion of the filing operation, and optionally a priming operation to remove any air from the syringe (for example by priming any such air back into the bulk fluid container or through a priming tube), the controller 900 may be programmed or configured to selectively actuate the bulk fluid valves 215A and 215B to block fluid communication between the respective syringes 10A, 10B and the bulk fluid container 19A, 19B via the bulk fluid paths 216A and 216B.

After the filling operation and priming operation, the controller 900 may be programmed or configured to execute a delivery operation during which the piston 13 associated with one or both of the syringes 10A, 10B is moved toward a distal end of the syringe to inject medical fluid F into the first fluid path 110A, 210A and the second fluid path 110B, 210B. The controller 900 may be programmed or configured to selectively actuate the bulk fluid valves 215A and 215B to establish fluid communication between the syringes 10A, 10B and the patient, via the fluid paths 110A, 110B, 210A, 210B. The first fluid path 110A, 210A and the second fluid path 110B, 210B ultimately merge into a patient fluid line 395, 495 in fluid communication with the vasculature of the patient. According to various embodiments, the first fluid path 110A, 210A and the second fluid path 110B, 210B may merge at a fluid mixing connector that provides turbulent mixing of the first fluid and the second fluid, such as a fluid mixing connector described in International PCT Application Nos. PCT/US2021/019507 and PCT/US2014/026324, the disclosures of which are incorporated herein by reference.

The controller 900 may be in operative communication with the at least one air detector 200 such that the controller 900 may stop actuation of the pistons 13 in response to the air detector 200 detecting the presence of one or more air bubbles in at least one of the first fluid path 110A, 210A and/or the second fluid path 110B, 210B. The controller 900 may further be in operative communication with at least one downstream automated remote shutoff valve 390, 490, such that the controller 900 may actuate the at least one remote shutoff valve 390, 490 to stop fluid flow and flow of the one or more air bubbles through the at least one remote shutoff valve 390, 490 and into the patient vascular system. The at least one remote shutoff valve 390, 490 may be actuated by the controller 900 between various positions such as delivery position in which medical fluid may flow to the patient, a stop position in which fluid flow to the patient is prevented, and a hemodynamic monitoring position in which the patient's vasculature is in fluid communication with a pressure transducer and isolated from syringes 10A, 10B.

During a normal delivery operation, the controller 900 may be programmed or configured to move the remote shutoff valve 390, 490, 590 to a delivery position to establish fluid communication between the patient and the fluid paths 110A, 110B, 210A, 210B. The controller 900 may be programmed or configured to transition the remote shutoff valve 390, 490 to a stop position in response to air being detected by the at least one air detector 200. In the stop position, the remote shutoff valve 390, 490 fluidly isolates the patient from the fluid paths 110A, 110B, 210A, 210B, thereby preventing air from being injected into the patient. Further details of the remote shutoff valve 390, 490 will be described in greater detail herein, for example with reference to FIGS. 3-5.

With continued reference to FIG. 2, in some embodiments, each of the first fluid path 110A, 210A and the second fluid path 110B, 210B may include a fluid path tubing element 230. Each fluid path tubing element 230 may be in the form of a zig-zag tubing element (as described in greater detail herein with reference to FIGS. 6-14) having a configuration to lengthen the fluid path distance between the at least one air detector 200 and the remote shutoff valve 390, 490 and increase fluid volume associated therewith. In some embodiments, the fluid path tubing element 230 may include a torturous path configured to at least temporarily trap or delay one or more air bubbles within the fluid path tubing element 230, for example by temporarily adhering to an inner wall surface or corner of the fluid path tubing element 230. In certain embodiments, the fluid path tubing element 230 may further include one or more widened sections having a greater cross-sectional area than a preceding section of the fluid path. The one or more widened sections may be configured to cause a fluid pressure drop within the fluid flow and to slow flow of the fluid through the widened sections, causing the one or more air bubbles to slow and/or temporarily adhere to an inner wall of the wider section of the tubing element. Various embodiments of the fluid path tubing element 230 are described in greater detail herein with reference to FIGS. 6-14. It is to be understood that not all embodiments of the fluid injector system 1000, 2000 include the fluid path tubing elements 230. For example, the embodiments shown in FIGS. 3 and 4 do not include the fluid path tubing elements 230.

In the embodiments of the fluid injector systems 1000, 2000 described herein, the at least one syringe 10A, 10B may be oriented in any manner such as upright, downright, or positioned at any degree angle. In certain embodiments the fluid injector system 1000, 2000 may be pivotable between one or more positions, for example, the fluid injector system 1000, 2000 may be positioned in an upright position during a filling operation and pivoted to a downward angled position during a delivery operation The injector system 1000, 2000 may be a multi-syringe injector, as shown, wherein several syringes 10A, 10B may be oriented side-by-side or in another spatial relationship and are separately actuated by respective pistons associated with the injector system 1000, 2000. However, it should be appreciated that the various embodiments described herein for preventing air injection to a patient are equally applicable to a single-syringe injector system.

Further details and examples of suitable nonlimiting powered injector systems, including syringes, controllers, and air detectors, are described in U.S. Pat. Nos. 5,383,858; 7,553,294; 7,666,169; 8,945,051; 10,022,493; and 10,507,319, the disclosures of which are hereby incorporated by reference in their entireties. While the fluid path elements described herein are illustrated in combination with a fluid injector system including syringes, other fluid delivery mechanisms, such as a pump, for example one or more peristaltic pumps, may be substituted for one or both of the syringes of the fluid delivery systems.

Figure 3:
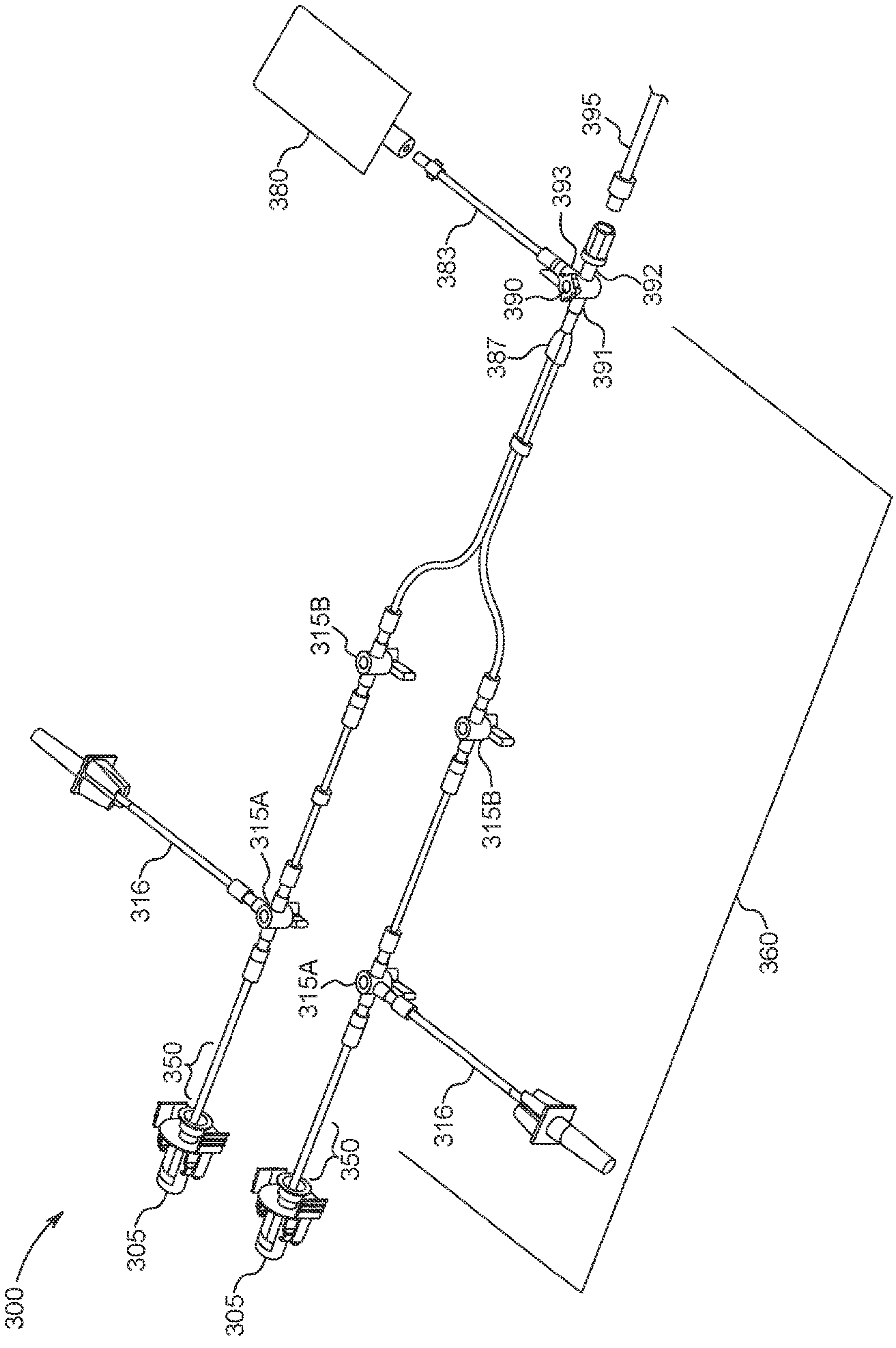
FIG. 3 is a perspective view of a fluid path assembly for use with a fluid injector system in accordance with an embodiment of the present disclosure.
Figure 4:
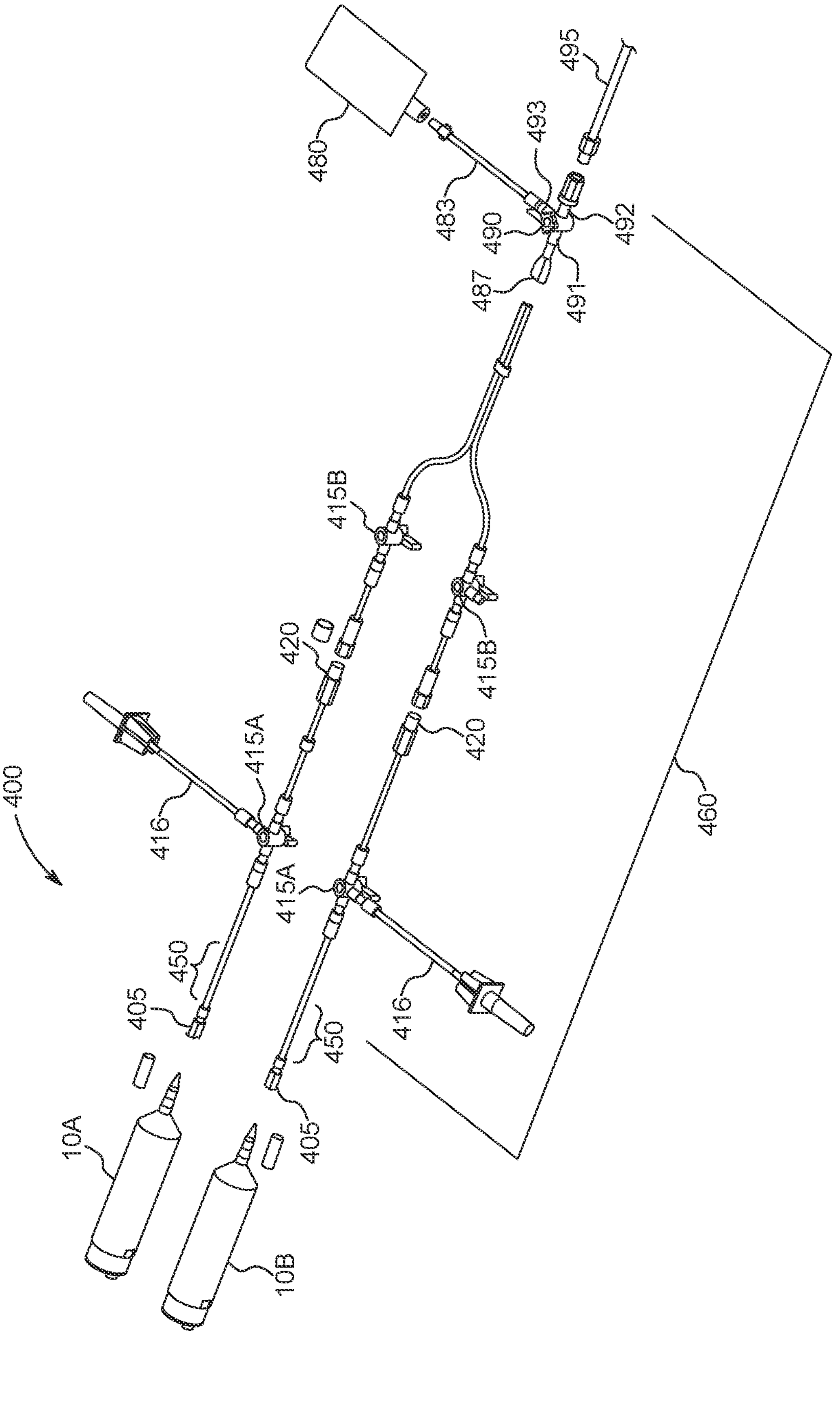
FIG. 4 is a perspective view of a fluid path assembly for use with a fluid injector system in accordance with an embodiment of the present disclosure.

Referring now to FIGS. 3 and 4, various embodiments of fluid path assemblies 300, 400 for use with the injector systems 1000, 2000 (see FIGS. 1A-1B and 2) are illustrated. The fluid paths 110A, 110B, 210A, 210B shown in FIGS. 1A-1B and 2 may correspond to proximal sections of the fluid path assemblies 300, 400 according to certain embodiments. Likewise, the bulk fluid valves 215A and 215B of FIGS. 1B and 2 may correspond to various valves 315A and 415A of the fluid path assemblies 300, 400. Referring first to FIG. 3, a single-patient fluid path assembly 300 is configured for attachment to one or more high-pressure syringes, such as the syringes 10A, 10B of the injector systems 1000, 2000 shown in FIGS. 1A-1B and 2, by proximal connectors 305. The fluid path assembly 300 includes a length of tubing 360, which may correspond to the first fluid path 110A and the second fluid path 110B. A proximal section of the length of tubing 360 may include an air bubble sensing region 350 in operative communication with the at least one air detector 200 (see FIGS. 1A-1B and 2). As such, the at least one air detector 200 can detect the presence of one or more air bubbles in the fluid path 300 as the fluid passes through the air bubble sensing region 350 during an injection procedure. The fluid path assembly 300 may further include three-way stopcocks 315A to provide fluid communication between bulk fluid containers 19A, 19B (see FIG. 2) and the syringes 10 by way of bulk fluid paths 316. Other stopcocks 315B may be included in the fluid path assembly 300 to control fluid flow, pressure, and backflow, as described herein. In various embodiments, the fluid path assembly 300 may include a fluid mixing connector element 387 to merge fluid flow from each of the syringes 10. The fluid mixing connector element 387 may include a mixing element such as described in International PCT Application Nos. PCT/US2021/019507 and PCT/US2014/026324.

Referring still to FIG. 3, the automated remote shutoff valve 390 may be located proximal to or distal to the fluid mixing connector element 387. According to various embodiments where the automated remote shutoff valve 390 is located distal to the fluid mixing connector element 387, the automated remote shutoff valve 390 may include an input port 391 in selective fluid communication with the fluid mixing connector element 387, a patient port 392 in selective fluid communication with patient delivery tubing 395, and a hemodynamic sensor port 393 in selective fluid communication with a hemodynamic monitor 380, such as a pressure transducer, through hemodynamic fluid path 383. As described herein with reference to FIG. 2, the remote shutoff valve 390 may be moved between the delivery position, the stop position, and the hemodynamic monitoring position.

In the delivery position, the remote shutoff valve 390 provides fluid communication between the input port 391 and the patient port 392. As such, fluid communication between the at least one syringe 10A, 10B and the patient through the fluid path assembly 300, including the length of tubing 360 and the patient delivery tubing 395, permits fluid flow from the at least one syringe 10A, 10B, through the fluid path assembly 300, through the automated remote shutoff valve 390, and into the patient delivery tubing 395. The fluid path assembly 300 may remain in the fluid delivery position until the total desired volume of medical fluid is delivered to the patient, at which time the controller 900 may cease actuation of the plungers 14 to halt fluid flow and also actuate the remote shutoff valve 390 to the closed position to prevent unwanted fluid flow from the system to the patient by loss of capacitance volume (e.g., relaxation of the expanded volume of fluid path components) of the fluid path assembly 300 in the absence of a pressurizing force. Further, the fluid path assembly 300 may remain in the fluid delivery position until at least one air bubble is detected in the air bubble sensing region 350, at which time the controller 900 may move the remote shutoff valve 390 to the stop position as described herein. In some embodiments, controller 900 may additionally close one or more of the three-way valves 315A and/or 315B once the desired volume of fluid has been delivered to the patient in order to prevent over-delivery due to capacitance and mechanical slack in the injector system 1000, 2000.

In the hemodynamic monitoring position, the remote shutoff valve 390 provides fluid communication between the hemodynamic sensor port 393 and the patient port 392. In the stop position, the remote shutoff valve 390 isolates the input port 391 from the patient port 392, such that there is no fluid communication between the input port 391 and the patient port 392. In some embodiments, the hemodynamic monitoring position may also act as the stop position because there is no fluid communication between the input port 391 and the patient port 392 in the hemodynamic monitoring position.

As described herein, a typical angiographic injection procedure may experience fluid pressures of up to, for example, 1200 psi during delivery of fluid to the patient. As pressure sensors suitable for use as the hemodynamic monitor 380 may be damaged by such high pressures, the hemodynamic sensor port 393 may be isolated from the inlet port 391 and the patient port 392 in the hemodynamic monitoring position of the remote shutoff valve 390. In some embodiments, the hemodynamic position of the remote shutoff valve 390 may be used during a low-pressure injection phase or a monitoring phase of an injection protocol, such as described in PCT International Publication No. WO 2018/218132, the disclosure of which is hereby incorporated by reference in their entireties.

Suitable structures for the automated remote shutoff valve 390 include, for example stopcocks, pinch valves, high crack pressure valves, check valves, solenoid valves, spool valves, gate valves, knife valves, and the like, including combinations of one or more of these valves. In some embodiments, the automated remote shutoff valve 390 may be a three-way high-pressure stopcock including a rotatable inner valve member.

In some embodiments, an intermediate stop position of the fluid path assembly 300 may be used, for example by moving one of the three-way valves 315A or 315B to a closed position to prevent pressurized backflow of fluid from a pressurized second syringe 10B into the fluid path assembly 300, a bulk fluid source 19A, 19B, and/or a first syringe 10A. In certain embodiments, the intermediate stop position may allow pre-pressurization of a medical fluid in one or more of syringes 10A, 10B prior to delivery of fluid from the fluid path assembly 300 during an injection procedure. This may have the advantage of taking up capacitance in the syringe and other upstream fluid path components and/or taking up mechanical slack in the injector system to provide a more accurate fluid delivery volume. In other embodiments, pre-pressurization of a medical fluid in syringe 10 may provide smoother pressure/flow transitions when switching between injection of a more viscous medical fluid and a less viscous medical fluid, such as contrast and saline, respectively. Examples of injection protocols using pre-pressurization to prevent fluid flow spikes during fluid transitions are described in International PCT Publication Nos. WO 2019/046260 and WO 2019/046259, the disclosures of which are incorporated herein by this reference. In other embodiments, the intermediate stop position may allow for detection of air within the syringe system by pressurization of the syringe contents prior to the injection protocol, as described in International PCT Publication No. WO 2019/204605, the disclosure of which is incorporated herein by this reference. In other embodiments, the intermediate stop position may allow for vacuum coalescences and purging of air bubbles from the syringe system prior to the injection protocol, as described in International PCT Publication No. WO 2019/204617, the disclosure of which is incorporated herein by this reference.

Referring now to FIG. 4, a multi-patient fluid path assembly 400 is configured for attachment to one or more high-pressure syringes, such as the syringes 10A, 10B of the injector systems 1000 shown in FIGS. 1A-1B, by proximal connectors 405. The fluid path assembly 400 includes a length of tubing 460, which may correspond to the first fluid path 210A and the second fluid path 210B. A proximal section of the length of tubing 460 may include an air bubble sensing region 450 in operative communication with the at least one air detector 200 (see FIGS. 1A, 1B, and 2). As such, the at least one air detector 200 can detect the presence of one or more air bubbles in the fluid path 400 as the fluid passes through the air bubble sensing region 450 during an injection procedure. The fluid path assembly 400 may further include three-way stopcocks 415A to provide fluid communication between bulk fluid containers 19A, 19B (see FIG. 2) and the syringes 10A, 10B by way of bulk fluid path 416. Other stopcocks 415B may be included in the fluid path assembly 400 to control fluid flow, pressure, and backflow, as described herein. In some embodiments, the fluid path assembly 400 may include a fluid mixing connector element 487 to merge fluid flow from each of the syringes 10 and ensure turbulent mixing of the two medical fluids. The fluid mixing connector element 487 may include a mixing element such as described herein.

Referring still to FIG. 4, the automated remote shutoff valve 490 may be located proximal to or distal to the fluid mixing connector element 487. According to various embodiments where the automated remote shutoff valve 490 is located distal to the fluid mixing connector element 487, the automated remote shutoff valve 490 may include an input port 491 in selective fluid communication with the fluid mixing connector element 487, a patient port 492 in selective fluid communication with a patient fluid line 495, and a hemodynamic sensor port 493 in selective fluid communication with a hemodynamic monitor 480, such as a hemodynamic pressure transducer, through hemodynamic fluid path 483. As described herein with reference to FIG. 2, the remote shutoff valve 490 may be moved between the delivery position, the stop position, and the hemodynamic monitoring position.

In the delivery position, the remote shutoff valve 490 provides fluid communication between the input port 491 and the patient port 492. As such, fluid communication between the at least one syringe 10A, 10B and the patient through the fluid path assembly 400, including the length of tubing 460 and the patient delivery tubing 495, permits fluid flow from the interior volume of the at least one syringe 10A, 10B, through the fluid path assembly 400, through the automated remote shutoff valve 490, and into the patient delivery tubing 495. The fluid path assembly 400 may remain in the fluid delivery position until the total desired volume of medical fluid is delivered to the patient, at which time the controller 900 may cease actuation of the plungers 13 to halt fluid flow and also actuate the remote shutoff valve 390 to the closed position to prevent unwanted fluid flow from the system to the patient by loss of capacitance volume (e.g., relaxation of the expanded volume of fluid path components) of the fluid path assembly 400 in the absence of a pressurizing force. Further, the fluid path assembly 400 may remain in the fluid delivery position until at least one air bubble is detected in the air bubble sensing region 450, at which time the controller 900 may move the remote shutoff valve 490 to the stop position as described herein. In some embodiments, controller 900 may additionally close one or more of the three-way valves 415A and/or 415B once the desired volume of fluid has been delivered to the patient in order to prevent over-delivery due to capacitance and mechanical slack in the injector system 1000, 2000.

In the hemodynamic monitoring position, the remote shutoff valve 490 provides fluid communication between the hemodynamic sensor port 493 and the patient port 492. In the stop position, the remote shutoff valve 490 isolates the input port 491 from the patient port 492, such that there is no fluid communication between the input port 491 and the patient port 492. In some embodiments, the hemodynamic monitoring position may also act as the stop position because there is no fluid communication between the input port 491 and the patient port 492 in the hemodynamic monitoring position.

As described herein, a typical angiographic injection procedure may experience fluid pressures of up to, for example, 1200 psi during delivery of fluid to the patient. As pressure sensors suitable for use as the hemodynamic monitor 480 may be damaged by such high pressures, the hemodynamic sensor port 493 may be isolated from the inlet port 491 and the patient port 492 in the hemodynamic monitoring position of the remote shutoff valve 490. In some embodiments, the hemodynamic position of the remote shutoff valve 490 may be used during a low-pressure injection phase or a monitoring phase of an injection protocol, such as described in PCT International Publication No. WO 2018/218132.

Suitable structures for the automated remote shutoff valve 490 include, for example stopcocks, pinch valves, high crack pressure valves, check valves, solenoid valves, spool valves, gate valves, knife valves, and the like, including combinations of one or more of these valves. In some embodiments, the automated remote shutoff valve 490 may be a three-way high-pressure stopcock including a rotatable inner valve member.

In some embodiments, an intermediate stop position of the fluid path assembly 400 may be used, for example by moving one of the three-way valves 415A or 415B to a closed position to prevent pressurized backflow of fluid from a pressurized second syringe 10*b* into the fluid path assembly 400, a bulk fluid source 19A, 19B, and/or a first syringe 10A. In certain embodiments, the intermediate stop position may allow pre-pressurization of a medical fluid in one or more of syringes 10A, 10B prior to delivery of fluid from the fluid path assembly 400 during an injection procedure. This may have the advantage of taking up capacitance in the syringe and other upstream fluid path components and/or taking up mechanical slack in the injector system to provide a more accurate fluid delivery volume. In other embodiments, pre-pressurization of a medical fluid in syringe 10 may provide smoother pressure/flow transitions when switching between injection of a more viscous medical fluid and a less viscous medical fluid, such as contrast and saline, respectively. Examples of injection protocols using pre-pressurization to prevent fluid flow spikes during fluid transitions are described in International PCT Publication Nos. WO 2019/046260 and WO 2019/046259. In other embodiments, the intermediate stop position may allow for detection of air within the syringe system by pressurization of the syringe contents prior to the injection protocol, as described in International PCT Publication No. WO 2019/204605. In other embodiments, the intermediate stop position may allow for vacuum coalescences and purging of air bubbles from the syringe system prior to an injection protocol, as described in International PCT Publication No. WO 2019/204617.

Referring again to FIGS. 1-4, the fluid injector system 1000 according to various embodiments may take from 60 milliseconds to 90 milliseconds, for example in one embodiment approximately 80 milliseconds, between when one or more air bubble is sensed in the air detection region by the at least one air detector to when the shutoff valve actuator may actuate the remote shutoff valve from the delivery position to the stop position to stop a high pressure (e.g. 1200 psi) injection procedure via actuation of the remote shutoff valve 390, 490. Total actuation time to stop such an injection procedure may include time detecting an air bubble by the air detector 200; time communicating from the air detector 200 to the controller 900 that an air bubble has been detected; time for the controller 900 actuating the remote shutoff valve 390, 490 to the stop position; and time until the patient line 395, 495 is fully isolated from the length of tubing 360, 460 to prevent continued fluid flow from one or more of rapid flow rate, compliance release, and/or bubble expansion from continuing into the patient's vasculature. At the high injection pressures typical of angiography injection procedures, an air bubble may move from 2.8 mL to 3.6 mL of the volume of the fluid path over the 70 milliseconds to 100 milliseconds between detection of the air bubble and valve closing/injection halting. For example, at approximately 1200 psi with conventional fluid path tubing diameters, an air bubble may travel a distance corresponding to 3.2 mL over 80 milliseconds at a flow rate of 30 mL/sec in a tubing with a 0.072 inch ID. The distance equivalence of 3.2 mL volume for such an embodiment may be approximately 1200 millimeters (or approximately 4 feet) of tubing length travelled during 80 milliseconds. Thus, even with a rapid response time, an air bubble may travel a significant distance after air detection and before system shutdown. Further, if pressurization of the fluid is halted or reduced, the reduction in fluid pressure may result in volume expansion of the air bubble, further increasing the distance the air volume can travel/occupy in the fluid path after a detection event. Thus, the volume of the tubing between the air detection region and remote shutoff valve 490 must be sufficient to allow the system adequate time to shut the fluid flow to the patient before the air bubble can pass the remote shutoff valve 490. The volume of the tubing may be a factor of one or more of inner tubing diameter, length of tubing, pliability or rigidity of the tubing, presence of one or more baffles and combinations thereof associated with the tubing.

According to various embodiments, the length of tubing 360, 460 may provide a sufficient overall length and/or volume between the air bubble detection region 350, 450 and the automated remote shutoff valve 390, 490 to ensure that an air bubble detected in the air detection region 350, 450 cannot inadvertently be injected into the patient. That is, the internal volume of the length of tubing 360, 460 is such that an air bubble detected in the air detection region 350, 450 has insufficient time to flow past the automated remote shutoff valve 390, 490 in the actuation time required for the fluid path assembly 300, 400 to reach the stop position. In some embodiments, the overall length and volume of the length of tubing 360, 460 between the air bubble detection region 350, 450 and the inlet port 391, 491 may be a length calculated to prevent the air bubble from moving into the patient tubing 395, 495 before the remote shutoff valve 390, 490 can reach the stop position. The air bubble will thus become trapped in the length of tubing 360, 460 by moving the remote shutoff valve 390, 490 to the stop position and the injection procedure is halted. In certain embodiments, the fluid path assembly 300, 400 between the air bubble detection region 350, 450 and the automated remote shutoff valve 390, 490 may have a length of between approximately 1000 millimeters and approximately 1400 millimeters, and in some embodiments may be approximately 1200 millimeters (or from approximately 3.5 feet to approximately 4.5 feet, and in specific embodiments may be approximately 4 feet) in length to ensure that air bubbles cannot flow into the patient delivery tubing 395, 495. The approximately 1000 millimeter to approximately 1400 millimeter length of tubing may be arranged in any manner between the air bubble detection region 350, 450 and the automated remote shutoff valve 390, 490, for example, may be stretched lengthwise, draped, wrapped, looped, or coiled to reduce the footprint of the tubing length.

Figure 5:
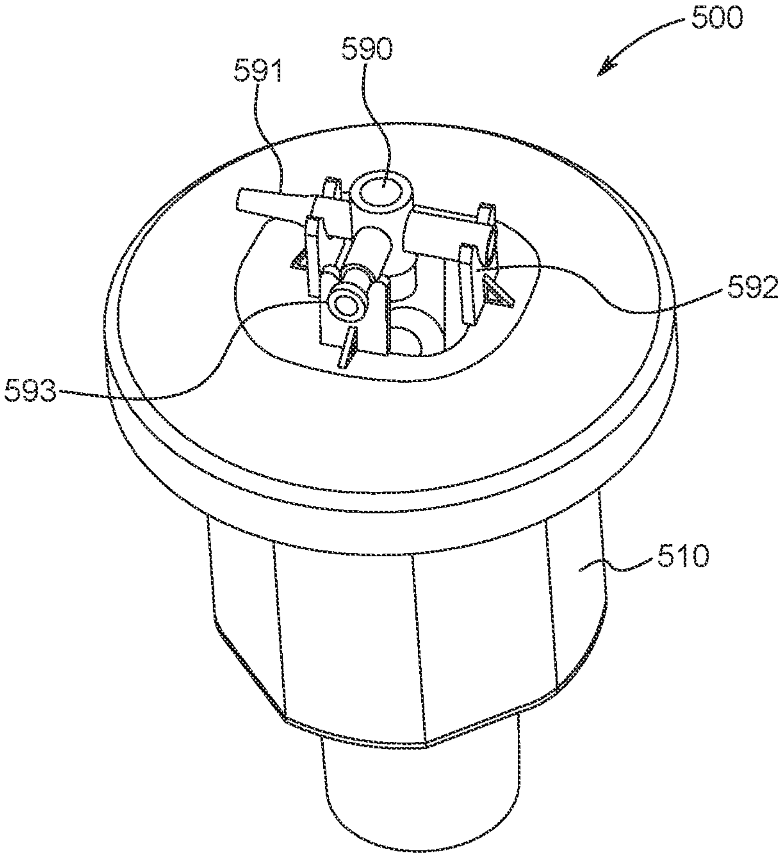
FIG. 5 is a perspective view of a remote automated shutoff valve for use with fluid path assembly of a fluid injector system in accordance with an embodiment of the present disclosure.

Referring now to FIG. 5, an embodiment of a remote valve assembly 500 including an automated remote shutoff valve 590 is illustrated. The remote shutoff valve 590 illustrated in FIG. 5 may correspond to the automated remote shutoff valve 390 or 490 of FIGS. 2-4, respectively. The remote valve assembly 500 includes an inlet port 591 configured for fluid communication with an upstream fluid path, such as the length of tubing 360 or 460 of FIGS. 3 and 4, and an outlet port 592 configured for fluid communication with a downstream fluid path component, such as the patient delivery tubing 395, 495 ultimately connected to the vasculature of the patient. In some embodiments, the valve assembly 500 further includes a hemodynamic monitoring port 593 configured for fluid communication with a pressure sensor, such as the hemodynamic monitor 380, 480 of FIGS. 3 and 4, respectively.

The remote valve assembly 500 further includes an actuator element 510, such as an electromechanical motor, in operative communication with the controller 900 (see FIG. 2). The actuator element 510 may be configured to move the remote shutoff valve 590 between the delivery position, stop position, and hemodynamic monitoring positions described herein upon receiving a signal from the controller 900. The controller may be programmed or configured to send the signal to the actuator element 510 in response to the air detector 200 determining the presence of at least one air bubble in the air bubble detection region 350, 450 (see FIGS. 3 and 4). Upon receipt of the signal from the controller 900, the actuator element 510 actuates the remote valve assembly 500 and moves the automated remote shutoff valve 590 from the delivery position to the stop position such that the inlet port 591 is isolated from the patient port 592, such that no fluid communication possible between the input port 591 and the patient port 592. In some embodiments, where the fluid injection protocol requires monitoring of the hemodynamic signal of the patient, the controller 900 may signal the actuator element 510 to move the automated remote shutoff valve 590 from the delivery position or the stop position to a hemodynamic monitoring position where fluid communication is provided between the hemodynamic monitoring port 593 and the patient port 592.

Referring now to FIGS. 6-14, embodiments of the present disclosure may include various fluid path tubing elements configured to lengthen and increase the volume of the fluid path between the air bubble sensing region 350, 450 and the remote shutoff valve 390, 490 (see FIGS. 2-4). The total length and/or volume of the fluid path tubing element may be determined by injection and apparatus parameters, such as flow rate, fluid viscosity, ID of tubing, and the actuation time of the remote shutoff valve 390, 490 as described herein. According to various embodiments, since the air bubbles are at least temporarily trapped or suspended in the fluid path tubing element upon moving the remote shutoff valve 390, 490 to the stop position, injection of air into the patient can be prevented. The various fluid path tubing elements may be configured to further reduce a footprint of the tubing between the air bubble sensing region 350, 450 and the remote shutoff valve 390, 490, for example to reduce the space occupied by the tubing in an injection suit, reduce packaging size, increase ease of handling, reduce disposal volume, increase ease of manufacture, etc.

Figure 6:
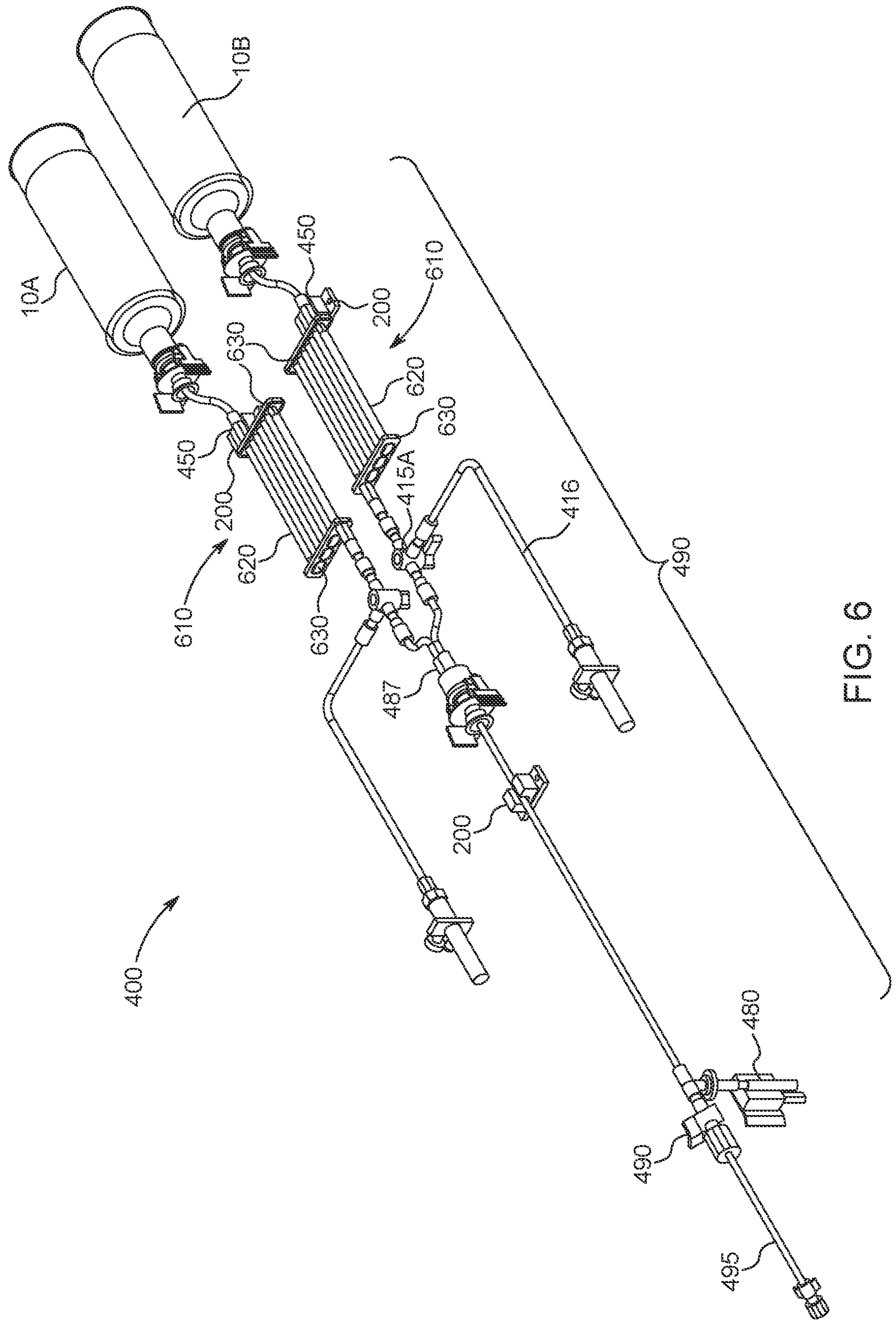
FIG. 6 is a perspective view of various single- or multi-use components for a fluid injector system according to an embodiment of the present disclosure.
Figure 7:
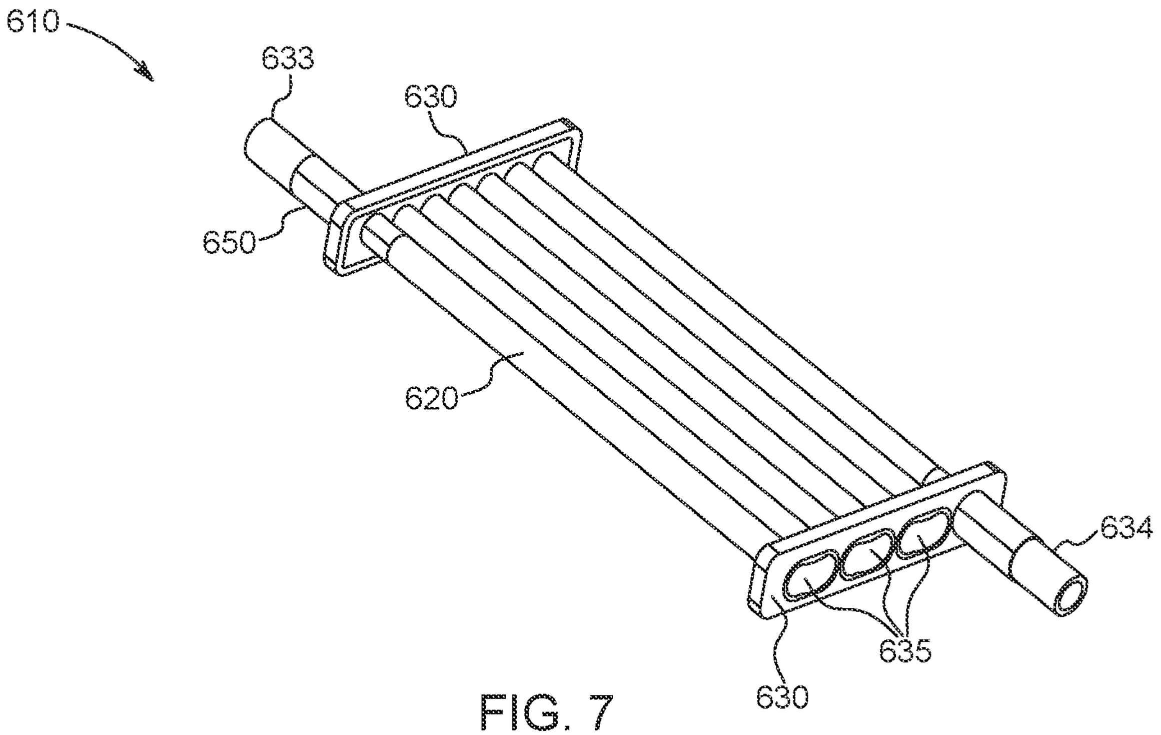
FIG. 7 is a perspective view of a fluid path tubing element of the fluid path assembly of FIG. 6 according to an embodiment of the present disclosure.

With reference to FIGS. 6-10, an embodiment of the fluid path assembly 400 according to the present disclosure includes a fluid path tubing element 610 associated with each of the syringes 10. For clarity, some of the components of the fluid path assembly 400 are not specifically identified in FIG. 6. However, the structure and function of such unidentified components are analogous to those described herein with reference to FIG. 4. The fluid path tubing element 610 is provided in at least a portion of the length of tubing 460 between the air detector 200 and the fluid mixing connector element 487. While FIG. 6 illustrates the fluid path tubing elements 610 upstream of the three-way stopcock 415A, in other embodiments, the fluid path tubing elements 610 may be located downstream of the three-way stopcock 415A, for example after the three-way stopcock 415A and before fluid mixing connector element 487.

With continued reference to FIG. 6 and further reference to FIGS. 7-10, the fluid path tubing element 610 may have a co-parallel, zig-zag fluid path configuration including a tubing portion 620 having a plurality of parallel individual tubes 622, and two end cap elements 630 configured to connect adjacent open ends of the tubing portion 620. The tubing portion 620 and the two end cap elements 630 may be formed from a medical grade polymer, metal, or composite material, such as rigid, non-compliant material, and may be formed by a molding process, such as injection molding. A total length and volume of the individual tubes 622 and tubing elements of the end cap elements 630 of the tubing portion 620 may be greater than the volume distance that an air bubble can travel or expand in the actuation time of the remote shutoff valve 490 after an air bubble detection event. As such, between the time at which air is detected in the air bubble sensing region 450 and the time at which the remote shutoff valve 390, 490 reaches the stop position subsequent to actuation by the controller 900, the air bubbles have insufficient time to travel the entire length and volume of tubing in the tubing portion 620 and are therefore isolated in the tubing portion 620 once the remote shutoff valve 490 is in the closed position. The air bubbles are thus contained within the fluid path tubing element 610. In certain embodiments, the plurality of individual tubes 622 of the tubing portion 620 may be substantially straight and parallel to one another, whereas in other embodiments, the individual tubes 622 may be in a configuration that is not parallel but nevertheless reduces the overall footprint of the tubing portion 620 and the fluid path tubing element 610. For example, the individual tubes 622 may be curved, spiral, circular, helical wavy, undulating, etc. In addition, although the plurality of individual tubes 622 are illustrated in a substantially co-planar orientation, in other embodiments, the plurality of individual tubes 622 may be arranged in a more 3-dimensional manner, for example as a block or other 3D arrangement of parallel tubes.

As described herein, the fluid injector system 1000, 2000 according to various embodiments of the present disclosure may take from 60 milliseconds to 90 milliseconds, for example in one embodiment approximately 80 milliseconds, to stop a high pressure (e.g. 1200 psi) injection procedure via actuation of the remote shutoff valve 390, 490. Total actuation time to stop such an injection procedure may include time detecting an air bubble by the air detector 200; time communicating to the controller 900 that an air bubble has been detected; time for the controller 900 actuating the remote shutoff valve 390, 490 to the stop position; and time until the patient delivery tubing 395, 495 is fully isolated from the length of tubing 360, 460 to prevent fluid continued fluid flow from one or more of rapid flow rate, compliance release, and/or bubble expansion from continuing into the patient. At the high injection pressures typical of CV injection procedures, an air bubble may move from 2.8 mL to 3.6 mL of the volume of the fluid path over the 70 milliseconds to 100 milliseconds between detection of the air bubble and valve closing/injection halting. For example, at approximately 1200 psi, an air bubble may travel a distance corresponding to 3.2 mL over 80 milliseconds at a flow rate of 30 mL/sec in a tubing with a 0.072 inch ID. The distance equivalence of 3.2 mL volume for such an embodiment may be approximately 1200 millimeters (or approximately 4 feet) of tubing length travelled during 80 milliseconds. Thus, even with a rapid response time, an air bubble may travel or expand a significant distance after air detection and before system shutdown.

Based on parameters such as tubing ID, the actuation time of the remote shutoff valve 390, 490, and other factors described herein, the total length of the individual tubes 622 may be selected to ensure that air bubbles have insufficient time to travel the entire length of tubing in the tubing portion 620 upon detection of the bubbles and actuation of the remote shutoff valve 390, 490. In some embodiments, the total fluid path length of the individual tubes 622 may be between approximately 1000 millimeters and approximately 1400 millimeters, and in some embodiments may be approximately 1200 millimeters (or between approximately 3.5 feet and approximately 4.5 feet, and in some embodiments may be approximately 4 feet) to ensure that air bubbles detected in the air detection region 650 are not injected into the patient.

With continued reference to FIGS. 6-10, the end caps 630 of the fluid path tubing element 610 may include an inlet port 633 or outlet port 634 for providing fluid communication to and from the fluid path tubing element 610. The inlet port 633 may be configured to provide fluid communication to the air bubble sensing region 450, and the outlet port 634 may be configured to provide fluid communication to a downstream portion of the length of tubing 460. The end caps 630 may include one or more u-turn elements 635 that connect the plurality of individual tubes 622 in series. For example, each of the u-turn elements 635 may define a 180° turn to divert fluid flow from one of the individual tubes 622 to an adjacent individual tube 622, creating a zig-zag pathway for the fluid flow through the fluid path tubing element 610 to form a fluid path from the inlet port 633 to the outlet port 634. Fluid may thus flow into the inlet port 633 of the fluid path tubing element 610 from the syringe 10, through all of the plurality of individual tubes 622 in series, and out of the outlet port 634 of the fluid path tubing element 610 toward the patient. In some embodiments, the total fluid path length of the individual tubes 622 and the u-turn elements 635 may be greater than a distance that an air bubble can travel or expand during the actuation time of the at least one shutoff valve 390, 490. In some embodiments, the total fluid path length of the individual tubes 622 and the u-turn elements 635 may be between approximately 1000 millimeters and approximately 1400 millimeters, and in some embodiments may be approximately 1200 millimeters (or between approximately 3.5 feet and approximately 4.5 feet, and in some embodiments may be approximately 4 feet) to ensure that air bubbles detected in the air detection region 650 are not injected into the patient.

Figure 8:
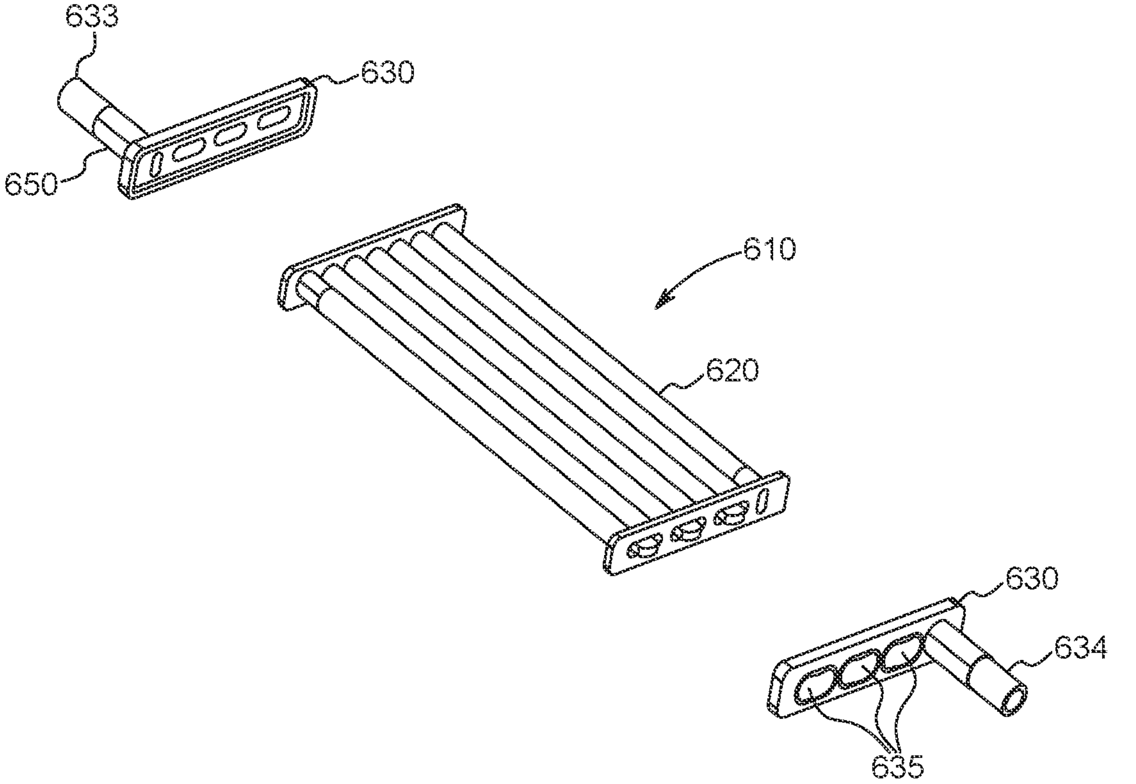
FIG. 8 is an exploded perspective view of the fluid path tubing element of FIG. 7.
Figure 9:
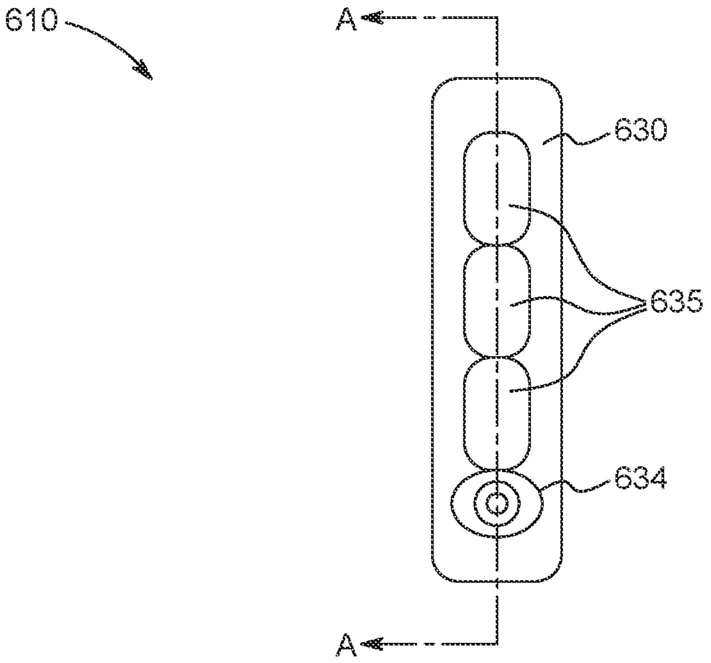
FIG. 9 is an end view of the fluid path tubing element of FIG. 7.
Figure 10:
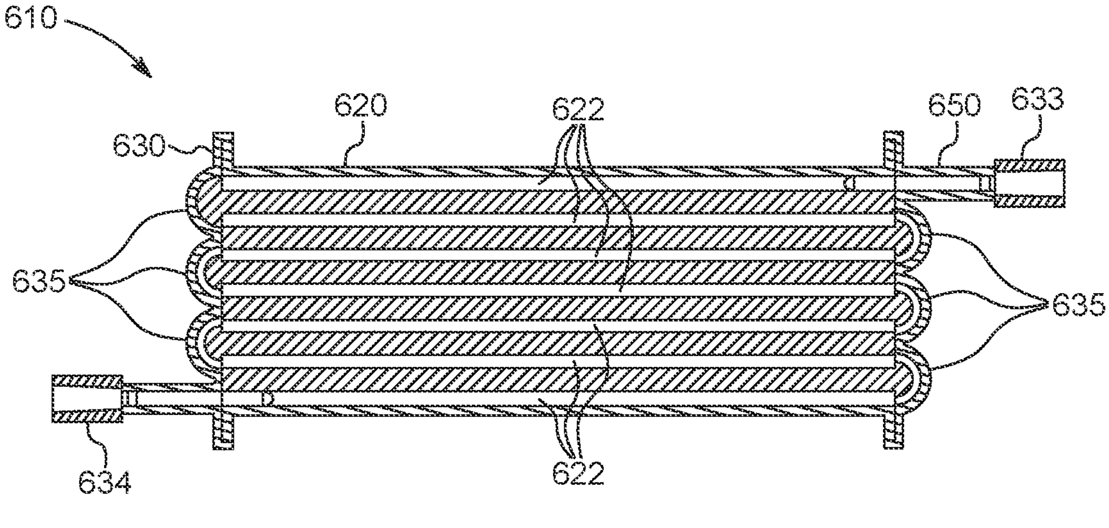
FIG. 10 is a cross-sectional side view of the fluid path tubing element of FIG. 7 along line A-A of FIG. 9.

Referring particularly to FIG. 8, the tubing portion 620 and the two end cap elements 630 may be manufactured as separate portions and then combined to form the fluid path tubing element 610. Manufacture as individual elements may be more readily accomplished during a molding process, such as an injection molding process, as removal of the molded elements from an injection mold may be simpler than attempting to mold the entire fluid path tubing element 610 in a single piece. The two end cap elements 630 may be bonded to opposing end of the tubing portion 620, for example by gluing, adhesion, welding, solvent welding, laser welding, and the like, such that the bonded connection may withstand the high pressures typical of angiography or other injection protocols (up to, e.g., 1200 psi). Other reinforcing features may be included to ensure non-separation of the two end cap elements 630 from the tubing portion 620.

In some embodiments, the inlet port 633 of the fluid path tubing element 610 may be configured to serve as the air bubble detecting region 450. In such embodiments, the inlet port 633 may include engagement features for directly interfacing with corresponding engagement features of the air detector 200, thereby holding the fluid path tubing element 610 in place relative to the injector housing 12 (see FIGS. 1A-2) and simplifying installation and setup of the fluid path assembly 400. Further, in certain embodiments, the inlet port 633 of the fluid path tubing element 610 including the air bubble detecting region 450 may be configured for direct connection with a distal fluid path outlet of a syringe 10. For example, the inlet port 633 may include a fluid path connector element such as connector element 305 (see FIG. 3), such as described in International PCT Application No. PCT/US2021/018523, the disclosure of which is incorporated by this reference in its entirety.

Figure 11:
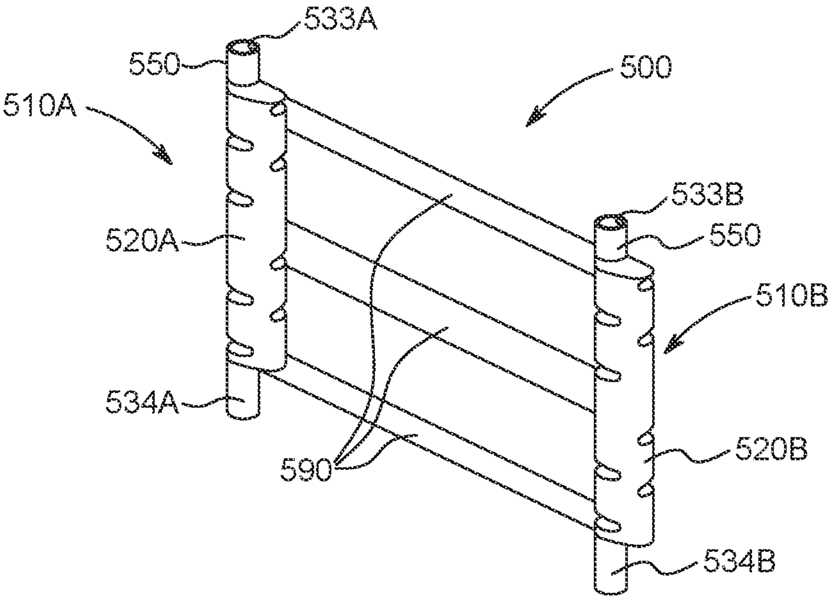
FIG. 11 is a side perspective view of a fluid path tubing element according to another embodiment of the present disclosure.
Figure 12:
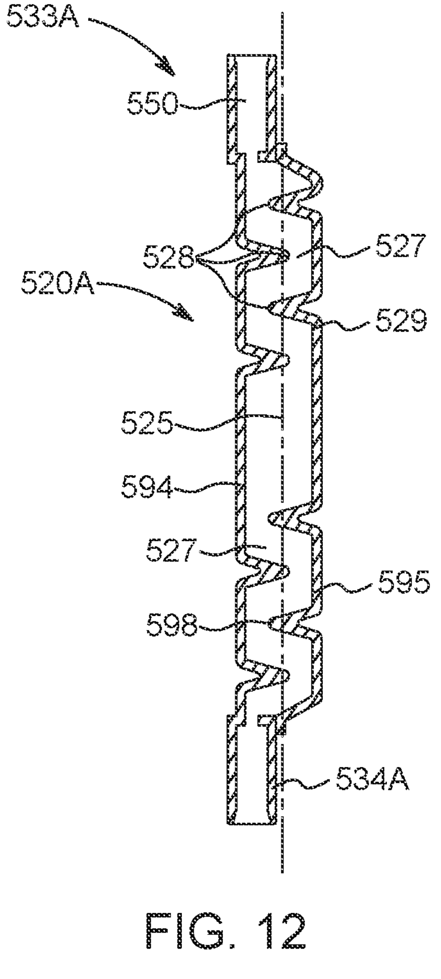
FIG. 12 is a cross-sectional side view of the fluid path tubing element of FIG. 11.

Referring now to FIGS. 11-12, another embodiment of the fluid path tubing element 500 is illustrated. The fluid path tubing element 500 includes at least one fluid path, for example a first fluid path 510A for a medical fluid, such as an imaging contrast media, and a second fluid path 510B for a flushing fluid, such as saline or Ringer's lactate. The first fluid path 510A and second fluid path 510B may be rigidly held by one or more support cross-members 590. The support cross-members 590 do not facilitate fluid flow, but rather may serve as a structural connection between the first fluid path 510A and second fluid path 510B to assist with installation and holding of the fluid path tubing element 500. The first fluid path 510A and second fluid path 510B include respective fluid inlets 533A, 533B and respective fluid outlets 534A, 534B to facilitate connection to various embodiments of the fluid path assemblies 300, 400 described herein. According to certain embodiments, each fluid inlet 533A, 533B of the fluid path tubing element 500 may include an air bubble detection region 550 configured for operative communication with the at least one air detector 200 (see e.g. FIGS. 1A, 1B, and 2). In such embodiments, the fluid inlets 533A, 533B may include engagement features for directly interfacing with corresponding engagement features of the at least one air detector 200, thereby holding the fluid path tubing element 500 in place relative to the injector housing 12 (see FIGS. 1A, 1B, and 2) and simplifying installation and setup of the fluid path assembly. The fluid outlets 534A, 534B may be configured for connection to the tubing downstream of the air detector 200 such that fluid injected from the syringes 10A, 10B enters the fluid path tubing element 500 at the fluid inlets 533A, 533B, flows through the fluid paths 510A, 510B, and exits via the fluid outlets 534A, 534B toward the patient.

FIG. 12 illustrates a cross-sectional view of fluid path 520A, from the fluid inlet 533A to fluid outlet 534A. Fluid path 520B may be identical, or may be a mirror image of fluid path 520A. Fluid paths 520A, 520B may include one or more fluid path configurations for disrupting fluid flow to facilitate air bubble retention within the fluid path tubing element 500. In some embodiments, fluid paths 520A, 520B may include torturous path sections 527 having a zig-zag configuration with switchback angles ranging from 160 to 180 degrees including corners for bubble isolation. In some embodiments, fluid paths 520A, 520B may include wider fluid path sections 525 having an increased cross-sectional area relative to preceding fluid path sections. According to certain embodiments, as fluid and air bubbles flow through the torturous path sections 527 and/or wider fluid path sections 525 of fluid paths 520A, 520B the air bubbles may temporarily adhere to an inner surface of the fluid path, thereby delaying their progress from the fluid inlet 533A to the fluid outlet 534A and providing additional time for the actuation of the remote shutoff valve 390, 490. Fluid path 520A may include a housing 594 in which the various features described herein are defined. The housing 594 may include a first side associated with a first inner surface 595 and a second side associated with a second inner surface 598 opposite the first inner surface 595. The first side associated with the first inner surface 595 and the second side associated with the second inner surface 598 may be formed separately from one another of a medical grade plastic, for example in an injection molding process or a printing process, and bonded to one another by gluing, adhesion, welding, solvent welding, laser welding, or the like. In some embodiments, the first side associated with the first inner surface 595 and the second side associated with the second inner surface 598 may be molded identical to one another, i.e. the first side associated with the first inner surface 595 and the second side 598 may be formed from the same mold. In other embodiments, the first side associated with the first inner surface 595 and the second side associated with the second inner surface 598 may be molded as mirror images of one another.

With continued reference to FIG. 12, the torturous path sections 527 may include a plurality of baffles 528 extending from the first inner surface 595 into the fluid path 520A and/or from the second inner surface 598 into the fluid path 520A. The plurality of baffles 528 are configured to disrupt laminar flow through the fluid path 520A, thereby decreasing the velocity at which air bubbles can flow through the tortious path section 527 and inducing the bubbles to adhere to the inner walls of the housing 594. In some embodiments, at least one baffle 528 extends from the first inner surface 595 of the housing 594 and at least one baffle 528 extends from the second inner surface 598 of the housing 594. In some embodiments, the at least one baffle 528 extending from the first inner surface 595 of the housing 594 is offset in a longitudinal direction from the at least one baffle 528 extending from the second inner surface 598 of the housing 594. In some embodiments, each of the plurality of baffles 528 extends across a longitudinal centerline CL of the housing 594. As such, fluid is forced to flow around the plurality of baffles 528 in order to advance toward the fluid outlet 534. In the embodiment shown in FIG. 12, each of the plurality of baffles 528 is generally triangular in shape, although other shapes are also considered within the scope of the present disclosure.

The plurality of baffles 528 may be configured to delay air bubble flow and/or trap certain air bubbles, such as small air bubbles, by adherence to corners 529 of the torturous path sections 527. In particular, the plurality of baffles 528 may be oriented to direct air bubbles into the corners 529 defined where the plurality of baffles 528 meet with the first inner surface 595 and/or the second inner surface 598 of the housing 594. Air bubbles of certain sizes may exhibit surface adhesion properties that cause such air bubbles to adhere to the housing 594 and/or the plurality of baffles 528 rather than be carried along the fluid path 520A with the medical fluid. As a result, the time that an air bubble travels through the torturous path sections 527 is increased, thereby providing additional actuation time for the controller and processor to actuate the remote shutoff valve 390, 490 and prevent flow of the air bubble through the valve to the patient.

In some embodiments, the fluid path 520A may include a widened portion 525 having an increased cross-sectional area relative to a preceding portion of the fluid path 520A. In some embodiments, the widened portion 525 may be located immediately downstream of one of the tortious path sections 527, which may have a diameter less than the diameter of the wide fluid channel 525. The increased diameter of the widened portion 525 may create a fluid pressure drop within the widened portion 525 as fluid flows into the widened portion 525. The fluid pressure drop may slow and/or stop flow of air bubbles through the widened portion 525 and promote surface adhesion of the air bubbles to an interior surface of the housing 594.

Figure 13:
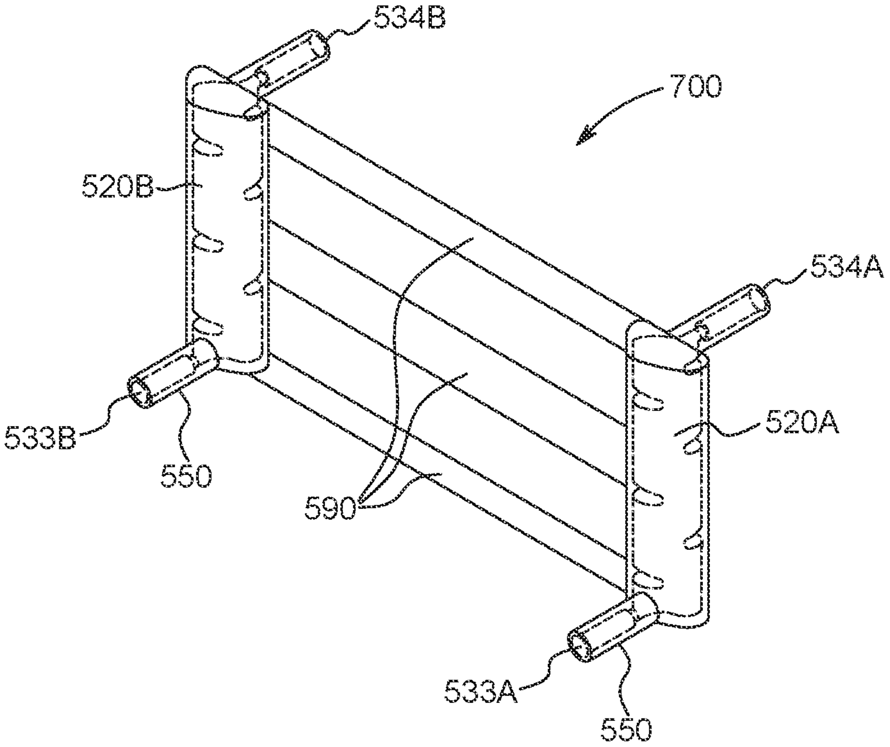
FIG. 13 is a side perspective view of a fluid path tubing element according to another embodiment of the present disclosure.
Figure 14:
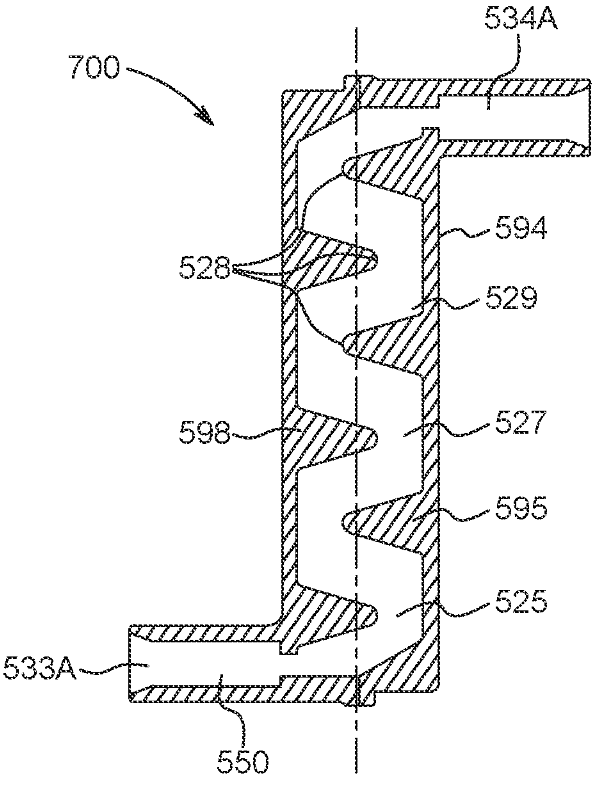
FIG. 14 is a cross-sectional side view of the fluid path tubing element of FIG. 13.

Referring now to FIGS. 13 and 14, another embodiment of a fluid path tubing element 700 in accordance with the present disclosure is substantially similar to the fluid path tubing element 500 of FIGS. 11-12, with like reference numerals corresponding to like parts. In contrast to the fluid path tubing element 500, the fluid inlets 533A, 533B and the fluid outlets 534A, 534B may be oriented at approximately 70° to approximately 90° relative to the longitudinal centerline CL of the housing 594.

In some embodiments, the fluid path tubing element 700 may be movable, such as by an actuator in operative communication with the controller 900 (see FIG. 2). During a priming operation, in which air is purged from the fluid injector system 1000, 2000 prior to an injection procedure, the fluid path tubing element 700 may be moved to a priming position illustrated in FIG. 14 such that fluid flows in the direction of arrow A. In the priming position, the fluid outlets 534A, 534B may be oriented spatially higher than the fluid inlets 533A, 533B. For example, the centerline CL of the housing 594 may be oriented substantially vertical. Because air is less dense than the medical fluid, any air bubbles in the fluid paths 520A, 520B may float upwards and further impelled towards the fluid outlets 534A, 534B during the priming operation. Thus, the buoyancy of the air bubbles, at least in part, causes the air bubbles to flow away toward the fluid outlets 534A, 534B in the priming position. The air bubbles may then be evacuated from the fluid path tubing element 700 by actuating the plungers 13 to purge air from the system 1000.

During a delivery operation, in which fluid is injected from the syringes 10 to the patient, the fluid path tubing element 700 may be moved to an injection position. In the injection position, the fluid inlets 533A, 533B may be oriented spatially higher than the fluid outlets 534A, 534B (i.e. a rotation of approximately 180° from the position shown in FIG. 14) For example, the centerline CL of the housing 594 may be oriented substantially vertical, but rotated approximately 180° relative to the priming position. Because air is less dense than the medical fluid, buoyancy directs any air bubbles in the fluid paths 520A, 520B upward away from the fluid outlets 534A, 534B. As such, the buoyancy of the air bubbles must be overcome by the force of the fluid flow in order for the air bubbles to reach the fluid outlets 534A, 534B. The buoyancy of the air bubbles therefore provides additional influence, in combination with volume effects and surface adhesion effects, for preventing the air bubbles from flowing out of the fluid outlets 534A, 534B toward the patient. Thus, the buoyancy of the air bubbles, at least in part, causes the air bubbles to flow away from the fluid outlets 534A, 534B in the injection position. The result may be an increased delay time of the one or more air bubble within the fluid path tubing element 700 therefore allowing additional time to actuate the remote shutoff valve 390, 490 by the controller.

Figure 15:
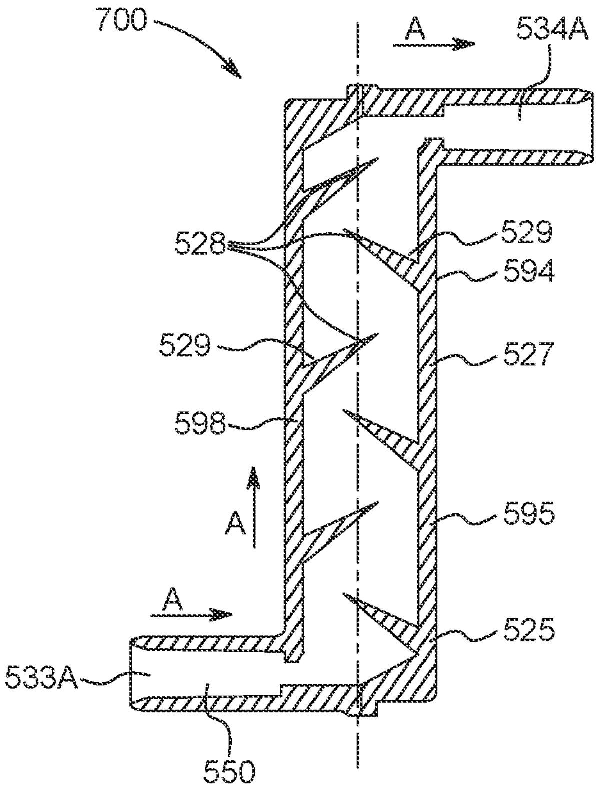
FIG. 15 is a cross-sectional side view of a fluid path tubing element according to another embodiment of the present disclosure; and Referring to the drawings in which like reference characters refer to like parts throughout the several views thereof, the present disclosure is generally directed to an in-line air bubble suspension apparatus for use with an angiography injector system.

Referring now to FIG. 15, another embodiment of the fluid path tubing set 700 is illustrated. In this embodiment, each of the plurality of baffles 528 has a directionality designed to enhance the ability of the fluid path tubing set 700 to trap air bubbles and increase adherence of the air bubble to an inner surface of the fluid path element 700. In particular, each of the baffles 528 extends from the first side 595 or the second side 598 of the housing 594 in a direction at least partially towards the fluid outlet 534A. When the fluid path tubing set 700 is moved to the priming position as shown in FIG. 15, any air bubbles present in the tortious path section 527 float upward toward the fluid outlet 534A. The baffles 528 may be angled such that air bubbles slide along the surfaces of the baffles 528 facing the fluid inlet 533A, progressively moving toward the fluid outlet 534A. The air bubbles may then be purged from the fluid outlet 534A as described herein.

Conversely, in the injection position of the fluid path tubing element 700, the angle of the baffles 528 directs air bubbles into corners 529 such that the air bubbles do not flow out of the housing 594. In the injection position of the fluid path tubing element 700 (i.e. approximately a 180° rotation from the priming position shown in FIG. 15), the buoyancy of air bubbles causes the air bubble to float upwards and become trapped in the acute corners 529, preventing the air bubbles from exiting the fluid path tubing set 700 via the fluid outlet 534A. Further, the air bubbles are held in corners 529 outside the force of the fluid flow such that the force of fluid flow does not dislodge the air bubbles by destroying the adhering force of the surface tension of the air bubble and the inner surface of the wall.

Based on parameters such as tubing ID, the actuation time of the remote shutoff valve 390, 490, and other factors described herein, the total length and/or volume of the fluid path tubing elements 500 and 700 of FIGS. 11-15 may be selected to ensure that air bubbles have insufficient time to travel the entire length and volume of the fluid path tubing elements 500 and 700 between detection of the bubbles and complete actuation of the remote shutoff valve 390, 490. In some embodiments, the total length of the fluid path tubing elements 500 and 700 may be between approximately 1000 millimeters and approximately 1400 millimeters, and in some embodiments may be approximately 1200 millimeters (or between approximately 3.5 feet and approximately 4.5 feet, and in some embodiments may be approximately 4 feet) to ensure that air bubbles detected in the air detection regions 550 are not injected into the patient. In another embodiment, the total volume of the fluid path tubing elements 500 and 700 may be greater than 2.8 mL, for example between approximately 2.8 mL to 3.6 mL of the volume and in some embodiments may be approximately 3.2 mL to ensure that air bubbles detected in the air detection regions 550 are not injected into the patient.

While various examples of the present disclosure were provided in the foregoing description, those skilled in the art may make modifications and alterations to these examples without departing from the scope and spirit of the disclosure. For example, it is to be understood that features of various embodiments described herein may be adapted to other embodiments described herein. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid injector system comprising:
at least one syringe configured for injecting medical fluid;
a fluid path assembly in fluid communication with the at least one syringe, the fluid path assembly comprising a plurality of individual parallel tubes and at least one air detection region;
an air detector configured to detect one or more air bubbles in a fluid path associated with the at least one air detection region;
at least one shutoff valve at a distal end of the fluid path assembly; and
at least one processor programmed or configured to actuate the at least one shutoff valve in response to the air detector detecting the one or more air bubbles in the fluid path associated with the air detection region to prevent fluid flow out of the fluid path assembly,
wherein the plurality of individual parallel tubes are connected to one another in series by a plurality of u-turn elements,
wherein the plurality of u-turn elements defines a 180° turn to divert fluid flow from one of the plurality of tubes to another of the plurality of individual parallel tubes,
wherein the plurality of u-turn elements are formed in a pair of end caps,
wherein the pair of end caps are joined to open ends of the plurality of individual parallel tubes to form a fluid path between an inlet port and an outlet port, and
wherein the fluid path assembly has a length greater than a distance that an air bubble can travel or expand during an actuation time of the at least one shutoff valve.

2. The fluid injector system of claim 1, wherein the actuation time of the at least one shutoff valve is a time interval between a time at which the air bubble is detected in the air detection region and a time at which the at least one shutoff valve reaches a stop position.

3. The fluid injector system of claim 1, wherein the fluid path assembly comprises a fluid path length having a path length of between approximately 1000 millimeters and approximately 1400 millimeters.

4. The fluid injector system of claim 1, wherein the plurality of individual parallel tubes are arranged in a zig-zag configuration.

5. The fluid injector system of claim 4, wherein the plurality of individual parallel tubes are parallel to one another.

6. The fluid injector system of claim 1, wherein the air detection region is associated with the inlet port of the fluid path assembly.

7. The fluid injector system of claim 1, wherein the fluid path assembly comprises a housing having a plurality of baffles to disrupt laminar flow of fluid through the housing.

8. The fluid injector system of claim 7, wherein the housing comprises a widened portion having an increased cross-sectional area configured to create a fluid pressure drop within the widened portion.

9. The fluid injector system of claim 7, wherein the plurality of baffles extend across a centerline of the housing such that fluid is forced to flow around the plurality of baffles.

10. The fluid injector system of claim 7, wherein the plurality of baffles comprises:
at least one baffle extending from a first inner surface into a fluid path of the housing; and
at least one baffle extending from a second inner surface into the fluid path of the housing and opposite of the first inner surface,
wherein the at least one baffle extending from the second inner surface of the housing is offset in a longitudinal direction from the at least one baffle extending from the first inner surface of the housing.

11. The fluid injector system of claim 1, wherein the fluid path assembly is movable between a priming position and an injection position,
wherein, in the priming position, an outlet of the fluid path assembly is oriented substantially upward such that the one or more air bubbles within the fluid path flow towards the outlet due, at least in part, to buoyancy, and
wherein, in the injection position, the outlet of the fluid path assembly is oriented downward such that the one or more air bubbles within the fluid path flow away from the outlet due, at least in part, to buoyancy.

12. The fluid injector system of claim 7, wherein the plurality of baffles extend at the outlet port least partially towards the outlet port.

13. A fluid path tubing element for a fluid injector system, the fluid path tubing element comprising:
an inlet port configured for fluid communication with at least one syringe;
an outlet port configured for fluid communication with a valve;
a tubing portion having a plurality of individual parallel tubes; and
a plurality of u-turn elements connecting the plurality of individual parallel tubes in series in a zig-zag-configuration,
wherein each of the plurality of u-turn elements defines a 180° turn to divert fluid flow from one of the plurality of tubes to another of the plurality of tubes, and
wherein the plurality of u-turn elements are formed in a pair of end caps, and wherein the pair of end caps are joined to open ends of the plurality of individual parallel tubes of the tubing portion to form a fluid path between the inlet port and the outlet port.

14. The fluid path tubing element of claim 13, wherein a total length of the fluid path tubing element is greater than a distance that an air bubble can travel or expand during an actuation time of the valve.

15. The fluid path tubing element of claim 13, wherein the inlet port comprises an air detection region configured for operative communication with an air detector configured to detect one or more air bubbles in the air detection region.

16. The fluid path tubing element of claim 13, wherein a total length of the fluid path of the fluid path tubing element is between approximately 1000 millimeters and approximately 1400 millimeters.

* * * * *